United States Patent
Imamura et al.

(10) Patent No.: US 11,940,630 B2
(45) Date of Patent: Mar. 26, 2024

(54) DISPLAY APPARATUS AND DISPLAY METHOD

(71) Applicant: SONY GROUP CORPORATION, Tokyo (JP)

(72) Inventors: Teppei Imamura, Tokyo (JP); Ryo Ogawa, Tokyo (JP); Masanori Iwasaki, Tokyo (JP); Takanobu Omata, Tokyo (JP); Katsuyuki Akutsu, Tokyo (JP); Itaru Shimizu, Tokyo (JP)

(73) Assignee: Sony Group Corporation, Tokyo (JP)

( * ) Notice: Subject to any disclaimer, the term of this patent is extended or adjusted under 35 U.S.C. 154(b) by 0 days.

(21) Appl. No.: 17/998,976

(22) PCT Filed: Apr. 19, 2021

(86) PCT No.: PCT/JP2021/015895
§ 371 (c)(1),
(2) Date: Nov. 16, 2022

(87) PCT Pub. No.: WO2021/241073
PCT Pub. Date: Dec. 2, 2021

(65) Prior Publication Data
US 2023/0213766 A1 Jul. 6, 2023

(30) Foreign Application Priority Data
May 27, 2020 (JP) .................. 2020-092553

(51) Int. Cl.
*G02B 27/01* (2006.01)
*G02B 5/32* (2006.01)
(Continued)

(52) U.S. Cl.
CPC .......... *G02B 27/0172* (2013.01); *G02B 5/32* (2013.01); *G02B 26/101* (2013.01);
(Continued)

(58) Field of Classification Search
CPC .. G02B 27/0172; G02B 27/0093; G02B 5/32; G02B 26/101; G02B 2027/0116; G02B 2027/0174
(Continued)

(56) References Cited

U.S. PATENT DOCUMENTS

| 2013/0083173 A1* | 4/2013 | Geisner ............... G02B 27/017 348/51 |
| 2013/0182302 A1* | 7/2013 | Shikii .................. H04N 9/3161 359/13 |

(Continued)

FOREIGN PATENT DOCUMENTS

| CN | 103140791 | 6/2013 |
| CN | 108780223 | 11/2018 |

(Continued)

OTHER PUBLICATIONS

International Search Report and Written Opinion prepared by the Japan Patent Office dated Jun. 7, 2021, for International Application No. PCT/JP2021/015895, 3 pgs.

*Primary Examiner* — Mark Edwards
(74) *Attorney, Agent, or Firm* — Sheridan Ross PC

(57) ABSTRACT

To provide a display apparatus that makes it possible to further improve a performance in controlling video presentation according to characteristics of an eyeball of a user. A display apparatus is provided that includes a light source; a processor that performs processing on a distribution of characteristics of an eyeball; a monitoring section that monitors a state of the eyeball; a matching section that performs matching on the distribution of the characteristics of the eyeball and the state of the eyeball; and an irradiator that irradiates a specified position on a retina with video display light emitted by the light source.

15 Claims, 13 Drawing Sheets

(51) Int. Cl.
*G02B 26/10* (2006.01)
*G02B 27/00* (2006.01)

(52) U.S. Cl.
CPC .. *G02B 27/0093* (2013.01); *G02B 2027/0116* (2013.01); *G02B 2027/0174* (2013.01)

(58) Field of Classification Search
USPC ............................................................ 345/8
See application file for complete search history.

(56) References Cited

U.S. PATENT DOCUMENTS

| | | | |
|---|---|---|---|
| 2017/0132757 A1 | 5/2017 | Thiebaud et al. | |
| 2017/0273558 A1 | 9/2017 | Tamura | |
| 2017/0277257 A1 | 9/2017 | Ota et al. | |
| 2018/0033405 A1* | 2/2018 | Tall | G06T 9/00 |
| 2018/0367769 A1 | 12/2018 | Greenberg | |
| 2019/0286229 A1 | 9/2019 | Chen et al. | |
| 2019/0324532 A1 | 10/2019 | Aleem et al. | |
| 2020/0064630 A1* | 2/2020 | Pfeiffer | G02B 27/0172 |
| 2020/0150443 A1* | 5/2020 | Ebert | G02B 27/0172 |

FOREIGN PATENT DOCUMENTS

| | | |
|---|---|---|
| CN | 109791605 | 5/2019 |
| CN | 110276239 | 9/2019 |
| EP | 2658074 | 10/2013 |
| EP | 3329316 | 6/2018 |
| EP | 3345125 | 7/2018 |
| EP | 3384337 | 10/2018 |
| EP | 3540574 | 9/2019 |
| JP | 2017-522591 | 8/2017 |
| JP | 2018-538573 | 12/2018 |
| JP | 2019-512726 | 5/2019 |
| JP | 2019-533325 | 11/2019 |
| JP | 2019-211705 | 12/2019 |
| KR | 2018-0115285 | 10/2018 |
| KR | 2019-0026030 | 3/2019 |
| TW | 2019-38104 | 10/2019 |
| WO | WO 2012/042793 | 4/2012 |
| WO | WO 2012/169064 | 12/2012 |
| WO | WO 2015/193287 | 12/2015 |
| WO | WO 2016/039187 | 3/2016 |
| WO | WO 2017/094002 | 6/2017 |
| WO | WO 2017/156486 | 9/2017 |
| WO | WO 2017/165035 | 9/2017 |
| WO | WO 2018/026730 | 2/2018 |
| WO | WO 2019/125575 | 6/2019 |
| WO | WO 2020/102132 | 5/2020 |

\* cited by examiner

DISPLAY APPARATUS AND DISPLAY METHOD

CROSS REFERENCE TO RELATED APPLICATIONS

This application is a national stage application under 35 U.S.C. 371 and claims the benefit of PCT Application No. PCT/JP2021/015895, having an international filing date of 19 Apr. 2021, which designated the United States, which PCT application claimed the benefit of Japanese Patent Application No. 2020-092553, filed 27 May 2020, the entire disclosures of each of which are incorporated herein by reference.

TECHNICAL FIELD

The present technology relates to a display apparatus and a display method.

BACKGROUND ART

In recent years, a technology that displays an image in a state of being superimposed on the scenery in the outside world such as an actual scene has attracted attention. This technology is also called augmented reality (AR). A head-mounted display is an example of products using such a technology. The head-mounted display is used by being worn on the head of a user. In a method for displaying a video (an image) using a head-mounted display, light from the head-mounted display reaches the eyes of a user in addition to light from the outside world, and this causes the user to recognize as if a video made up of light from the display is superimposed on an image in the outside world.

For example, Patent Literature 1 has proposed an image display apparatus that can detect a position, on a retina, onto which light irradiated by a light source is irradiated, and can adjust the irradiation position on the retina.

CITATION LIST

Patent Literature

Patent Literature 1: WO2012/169064

DISCLOSURE OF INVENTION

Technical Problem

However, there is a possibility that the technology proposed in Patent Literature 1 will not make it possible to further improve a performance in controlling video presentation according to characteristics of an eyeball of a user.

Thus, the present technology has been made in view of the circumstances described above, and it is a primary object of the present technology to provide a display apparatus and a display method that make it possible to further improve a performance in controlling video presentation according to characteristics of an eyeball of a user.

Solution to Problem

The inventors have conducted intensive researches in order to achieve the object described above. Consequently, the inventors have been surprisingly successful in further improving a performance in controlling video presentation according to characteristics of an eyeball of a user, and have completed the present technology.

In other words, the present technology provides, as a first aspect, a display apparatus that includes
a light source;
a processor that performs processing on a distribution of characteristics of an eyeball;
a monitoring section that monitors a state of the eyeball;
a matching section that performs matching on the distribution of the characteristics of the eyeball and the state of the eyeball; and
an irradiator that irradiates a specified position on a retina with video display light emitted by the light source.

The display apparatus of the first aspect according to the present technology may further include
an acquisition section that acquires the distribution of the characteristics of the eyeball.

In this case, the acquisition section may include at least one selected from the group consisting of a fundus camera, an OCT, a refractometer, and a light detection apparatus that detects light that returns due to IR scanning.

In the display apparatus of the first aspect according to the present technology,
the monitoring section may monitor the state of the eyeball using a corneal reflex or a fundus reflex.

The display apparatus of the first aspect according to the present technology may further include
a follower that causes the video display light to follow a movement of the eyeball.

In this case, the follower may include at least one selected from the group consisting of a combiner, a relay-system drive section, a mirror drive section, and a phase difference panel.

In the display apparatus of the first aspect according to the present technology,
a coordinate system may be defined on the basis of the distribution of the characteristics of the eyeball.

In this case, using the coordinate system, the matching section may perform matching on the distribution of the characteristics of the eyeball and the state of the eyeball to which a video is to be presented.

The coordinate system may be defined on the basis of at least two selected from the group consisting of a right-eye first fovea, a right-eye first blind spot, a left-eye second fovea, and a left-eye second blind spot.

In the display apparatus of the first aspect according to the present technology,
the light source may be a laser source.

The display apparatus of the first aspect according to the present technology may further include
a scanning mirror, and
the scanning mirror may irradiate the video display light onto the retina.

In the display apparatus of the first aspect according to the present technology,
the irradiator may further include a member arranged in front of eyes, and
the member may be a see-through member.

In this case, the member may be a first optical element or a second optical element, the first optical element including a reflective or transmissive volume hologram, a reflective or transmissive relief hologram, or a meta-surface, the second optical element being an optical element off which specified light is reflected and through which light other than the specified light is transmitted.

The display apparatus of the first aspect according to the present technology may further include a member for compensating for a wavelength dispersion.

In this case, the member for compensating for a wavelength dispersion may be a first optical element that includes a reflective or transmissive volume hologram, a reflective or transmissive relief hologram, or a meta-surface.

Further, the present technology provides, as a second aspect, a display method that includes performing processing on a distribution of characteristics of an eyeball;

monitoring a state of the eyeball;

performing matching on the distribution of the characteristics of the eyeball and the state of the eyeball; and irradiating a specified position on a retina with video display light emitted by a light source.

The display method of the second aspect according to the present technology may further include acquiring the distribution of the characteristics of the eyeball.

The present technology makes it possible to further improve a performance in controlling video presentation according to characteristics of an eyeball of a user. Note that the effects described here are not necessarily limitative, and any of the effects described in the present disclosure may be provided.

MODE(S) FOR CARRYING OUT THE INVENTION

Figure 1:
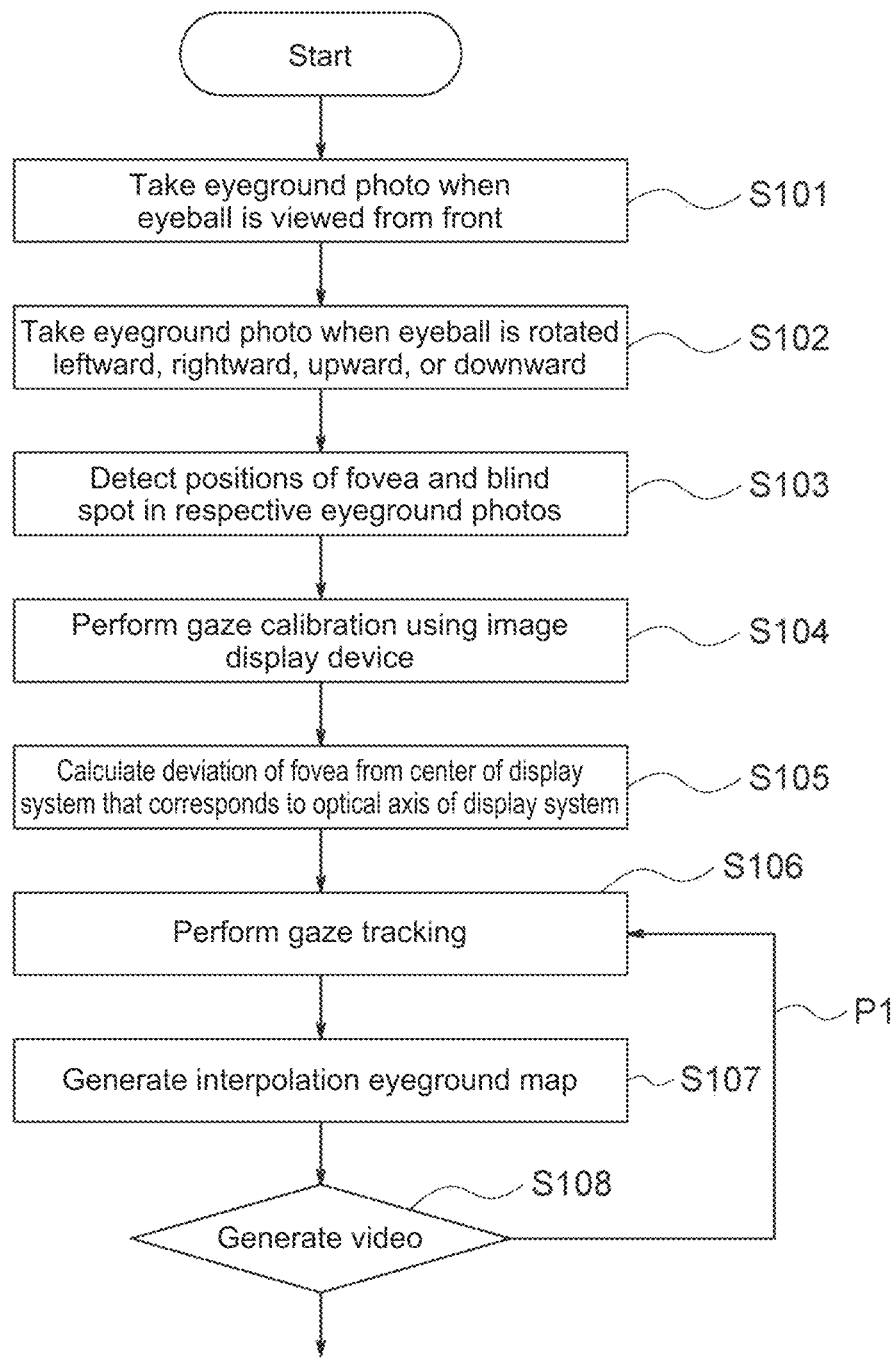
FIG. 1 illustrates an example of a flow of displaying a video using a display apparatus to which the present technology has been applied.

Favorable embodiments for carrying out the present technology will now be described below. Embodiments described below are examples of representative embodiments of the present technology, and the scope of the present technology is not construed as being limited to the embodiments. Note that, in the description with reference to the drawings, similar or equivalent elements or members are denoted by a similar reference numeral to omit a repetitive description.

Note that the description is made in the following order.
1. Overview of Present Technology
2. First Embodiment (First Example of Display Apparatus)
3. Second Embodiment (Second Example of Display Apparatus)
4. Third Embodiment (First Example of Display Method)
5. Fourth Embodiment (Second Example of Display Method)

1. Overview of Present Technology

First, an overview of the present technology is described. The present technology relates to a display apparatus and a display method.

According to the present technology, a distribution of characteristics of an eyeball (a shape and optical characteristics) is acquired, and matching is performed on coordinates defined on the distribution and a result of eye sensing. This makes it possible to display a video at a specified position on a retina according to the distribution of characteristics of an eyeball.

First, examples of technologies other than the present technology are described.

As a first example of the other technologies, there is an example of a technology related to planar-display-panel expanding eyewear. In the first example technology, a focal plane is fixed. Thus, there is a possibility that a stimulated portion on a retina will not be precisely specified. Further, as a second example of the other technologies, there is an example of a technology related to direct projection of an image onto a retina using laser. In the second example technology, a see-through performance is decreased when a half mirror is used, and this may result in unsuitableness for attracting attention to an object in the outside world. Further, an angle of view is made narrower and a wavelength dispersion occurs when a holographic optical element (HOE) is used, and this may result in difficulty in presenting a range of a stimulus and the accuracy in the stimulus. Furthermore, as a third example of the other technologies, there is an example of a technology related to a positional adjustment (following). In the third example technology, the positional adjustment may be performed using pattern matching (here, the pattern refers to, for example, a retinal pattern regarding, for example, blood). Thus, reference data is large, and this may result in intensive processing.

The present technology has been made in view of the circumstances described above.

The present technology makes it possible to further improve a performance in controlling video presentation according to characteristics of an eyeball of a user. Further, the present technology also makes it possible to further improve a performance in controlling video presentation according to a movement of an eyeball (an ocular movement) of a user.

Specifically, in the present technology, information regarding a distribution of characteristics of an eyeball is acquired, a coordinate system is defined, and a displayed video and a display position are defined in the coordinate system. This results in smaller volumes of data, compared to when a pattern map is used. Further, a displayed video (a presented video) and a display position (a presentation position) are controlled on the basis of information regarding a movement of an eyeball (such as information regarding a rotation of an eyeball). This results in less intensive processing, compared to when pattern matching is used. For example, the coordinate system is defined on the basis of at least two selected from the group consisting of a right-eye fovea (the right-eye fovea may be referred to as a first fovea), a right-eye blind spot (the right-eye blind spot may be referred to as a first blind spot), a left-eye second fovea (the left-eye fovea may be referred to as a second fovea), and a left-eye second blind spot (the left-eye blind spot may be referred to as a second blind spot).

Further, in the present technology, a stimulus of a specific wavelength can be presented since a laser source is favorably used. Further, it is possible to gaze at an object in the outside world and to present an unconsciously provided stimulus, since a member arranged in front of the eyes is favorably a see-through member. Furthermore, a wavelength dispersion can be compensated for since a member for compensating for a wavelength dispersion is favorably used, and thus a specified point (any point) on a retina can be precisely stimulated.

Examples of the member arranged in front of the eyes include a first optical element and a second optical element, the first optical element including a reflective or transmissive volume hologram, a reflective or transmissive relief hologram, or a meta-surface, the second optical element being an optical element off which specified light is reflected and through which light other than the specified light is transmitted. For example, the first optical element including a meta-surface may have, on the surface of the first optical element, a structure in which dielectrics or metals are periodically narrowly spaced from each other, and can deflect light of a specific frequency band.

Examples of the second optical element include a half mirror (of which light transmittance is favorably 50% or more), a bandpass filter off which only a specific wavelength (a wavelength of a light source) is reflected and through which a wavelength other than the specific wavelength is transmitted, and a polarizing beam splitter off which specific polarized light is reflected.

Examples of the member for compensating for a wavelength dispersion include the first optical element including a reflective or transmissive volume hologram, a reflective or transmissive relief hologram, or a meta-surface. For example, as described above, the first optical element including a meta-surface and serving as the member for compensating for a wavelength dispersion may also have, on the surface of the first optical element, a structure in which dielectrics or metals are periodically narrowly spaced from each other, and can deflect light of a specific frequency band.

Favorable embodiments for carrying out the present technology will now be described in detail below with reference to the drawings. Embodiments described below are examples of representative embodiments of the present technology, and the scope of the present technology is not construed as being limited to the embodiments.

2. First Embodiment (First Example of Display Apparatus)

A display apparatus of a first embodiment according to the present technology (a first example of a display apparatus) is a display apparatus that includes a light source, a processor that performs processing on a distribution of characteristics of an eyeball, a monitoring section that monitors a state of the eyeball, a matching section that performs matching on the distribution of the characteristics of the eyeball and the state of the eyeball, and an irradiator that irradiates a specified position on a retina with video display light emitted by the light source. The display apparatus of the first embodiment according to the present technology may further include a follower. The display apparatus of the first embodiment according to the present technology can be applied to, for example, an eyewear display and a head-mounted display.

The processor performing processing on a distribution of characteristics of an eyeball performs processing on, for example, information regarding a distribution of characteristics of an eyeball, the information regarding a distribution of characteristics of an eyeball being obtained from an external apparatus (such as a fundus camera, an OCT, a light detection apparatus that detects light that returns due to IR scanning, or a refractometer). The monitoring section monitors a state of an eyeball using, for example, a corneal reflex or a fundus reflex, and can acquire an optical axis. The matching section acquires a deviation of a visual axis from the optical axis (gaze calibration), and can generate a map in which an offset is reflected. The irradiator can modulate light depending on the laser source, display of a video (a projector), and a distribution of characteristics of an eyeball, can adjust a light amount depending on external light, and can perform control including distortion correction. The follower can cause a displayed video to follow an ocular movement due to eye tracking, where a light ray is steered to change an irradiated video and an irradiation position on the basis of information regarding a rotation of an eyeball.

First, an example of a flow of displaying a video using the display apparatus of the first embodiment according to the present technology is described with reference to FIG. 1.

An eyeground map is created in Steps S101 to S103 illustrated in FIG. 1. In more detail, an eyeground photo when an eyeball is viewed from the front is taken using, for example, a fundus camera in Step S101, and an eyeground photo when the eyeball is rotated leftward, rightward, upward, or downward using, for example, a fundus camera in Step S102. In Step S103, positions of a fovea and a blind spot in the respective eyeground photos taken in Steps S101 and S102 are detected.

Figure 2:
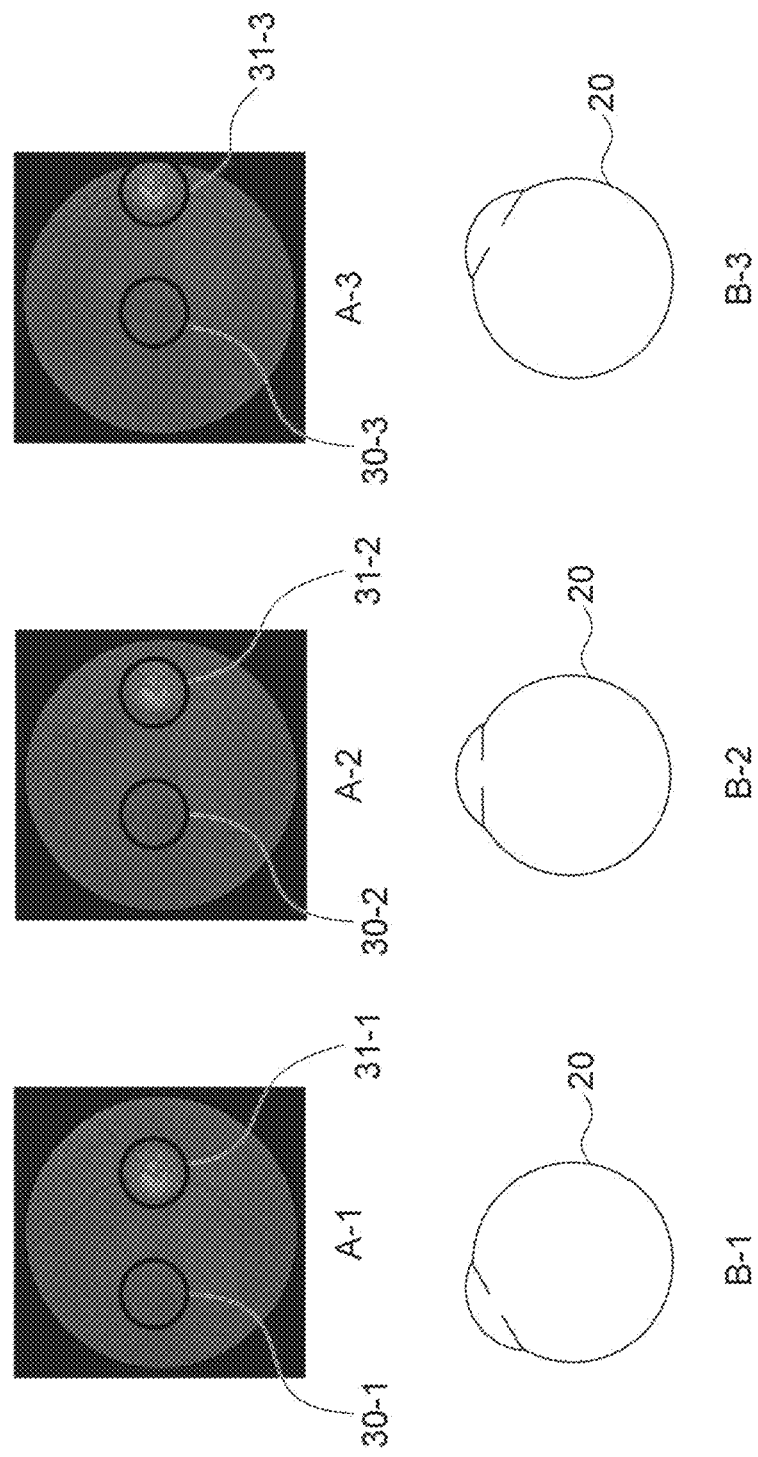
FIG. 2 is a diagram used to describe a change in positions of a fovea and a blind spot with leftward or rightward rotation of an eyeball of a right eye.

Steps S101 to S103 are specifically described with reference to FIG. 2. FIG. 2 is a diagram used to describe a change in positions of a fovea and a blind spot with leftward or rightward rotation of an eyeball of a right eye. In FIG. 2, A-2 of FIG. 2 illustrates an eyeground photo of a right eye as viewed from the front in Step S101, and B-2 of FIG. 2 is a top view schematically illustrating an eyeball 20 of the right eye as viewed from the front. In FIG. 2, A-1 of FIG. 2 illustrates an eyeground photo of the right eye when the eyeball 20 is rotated leftward in Step S102, and B-1 of FIG. 2 is a top view schematically illustrating the eyeball 20 of the right eye when the eyeball is rotated leftward. In FIG. 2, A-3 of FIG. 2 illustrates an eyeground photo of the right eye when the eyeball 20 is rotated rightward in Step S102, and B-3 of FIG. 2 is a top view schematically illustrating the eyeball 20 of the right eye when the eyeball is rotated rightward.

When A-1 and A-2 of FIG. 2 are compared, a fovea 30-1 illustrated in A-1 of FIG. 2 is moved leftward relative to a fovea 30-2 illustrated in A-2 of FIG. 2. Likewise, a blind spot 31-1 illustrated in A-1 of FIG. 2 is moved leftward relative to a blind spot 31-2 illustrated in A-2 of FIG. 2.

Note that a positional relationship between the fovea 30-2 and the blind spot 31-2 (a distance between the fovea 30-2 and the blind spot 31-2) in A-2 of FIG. 2, and a positional relationship between the fovea 30-1 and the blind spot 31-1 (a distance between the fovea 30-1 and the blind spot 31-1) in A-1 of FIG. 2 are substantially identical to each other.

When A-3 and A-2 of FIG. 2 are compared, a fovea 30-3 illustrated in A-3 of FIG. 2 is moved rightward relative to the fovea 30-2 illustrated in A-2 of FIG. 2. Likewise, a blind spot 31-3 illustrated in A-3 of FIG. 2 is moved rightward relative to the blind spot 31-2 illustrated in A-2 of FIG. 2.

Note that a positional relationship between the fovea 30-2 and the blind spot 31-2 (a distance between the fovea 30-2 and the blind spot 31-2) in A-2 of FIG. 2, and a positional relationship between the fovea 30-3 and the blind spot 31-3 (a distance between the fovea 30-3 and the blind spot 31-3) in A-3 of FIG. 2 are substantially identical to each other.

Matching is performed on a result of eye sensing (eye tracking) and an eyeground map in Steps S104 and S105 illustrated in FIG. 1. In more detail, gaze calibration is performed using the display apparatus of the first embodiment according to the present technology in Step S104, and a deviation of a fovea from a center of a display system that corresponds to an optical axis of the display system is calculated in Step S105.

Figure 3:
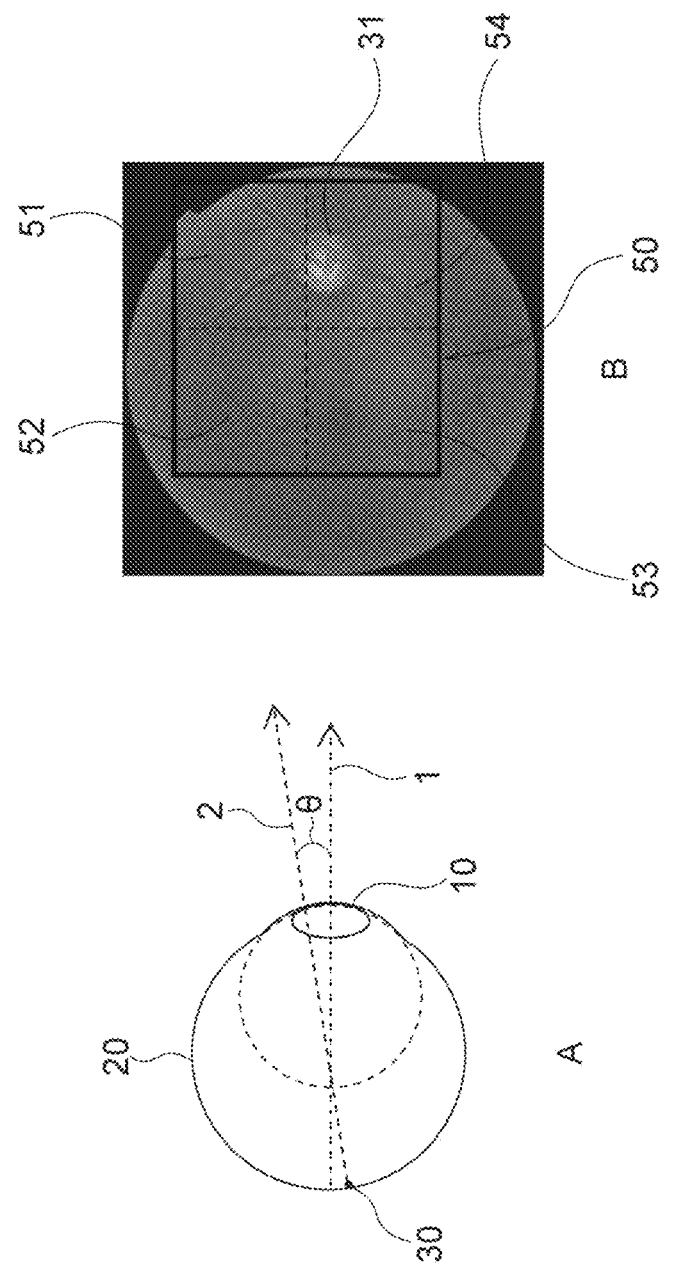
FIG. 3 is a diagram used to describe a result of matching performed on an eyeground map and a state of an eyeball to which a video is to be presented.

Steps S104 and 105 are specifically described with reference to FIG. 3. FIG. 3 is a diagram used to describe a result of matching performed on an eyeground map and a state of an eyeball to which a video is to be presented. As illustrated in A of FIG. 3, a visual axis (a gaze vector) 2 is deviated from an optical axis 1 (an optical vector) by an angle θ. The optical axis 1 is a normal to a cornea that passes through the center of a pupil 10, and the visual axis 2 is an axis that connects a nodal point (a central posterior surface of a lens) and a fovea 30.

From among a first quadrant 51 (for example, a region in which an X axis is in a positive direction and a Y axis is in a positive direction), a second quadrant 52 (for example, a region in which the X axis is in a negative direction and the Y axis is in the positive direction), a third quadrant 53 (for example, a region in which the X axis is in the negative direction and the Y axis is in a negative direction), and a fourth quadrant 54 (for example, a region in which the X axis is in the positive direction and the Y axis is in the negative direction) that form a video display range (angle of view) 50, a blind spot 31 extends into the first quadrant 51 and the fourth quadrant 54, as illustrated in B of FIG. 3.

Steps S106 to S108 illustrated in FIG. 1 are performed in a state in which a video is presented. In more detail, gaze tracking (line-of-sight tracking) is performed in Step S106. For example, in Step S106, a movement of an eyeball is followed, a position of a pupil is detected, and an angle of view of a desired point is calculated. Infrared light is caused to coincide with an optical axis used for image projection, and a fundus reflex (the reflectance at a position of a blind spot and the reflectance at a position of a fovea are different.) is detected. In Step S107, an interpolation eyeground map is generated. The interpolation eyeground map is generated by interpolating a leftward rotation, a rightward rotation, an upward rotation, and a downward rotation of an eyeball. For example, positions of a fovea and a blind spot when levels of a leftward rotation, a rightward rotation, an upward rotation, and a downward rotation of an eyeball are lower than levels of a leftward rotation, a rightward rotation, an upward rotation, and a downward rotation of the eyeball that are used for an eyeground map generated in Steps S101 to S103 are estimated using the eyeground map to generate the interpolation eyeground map. Note that the interpolation eyeground map may be generated using information regarding a position of a specific eyeball, or information regarding a shift of an angle of view. Then, a video is generated in Step S108. After the video is generated, a signal of the generated video is transmitted to a video display section that includes, for example, a light source (such as a laser source), a mirror, a scanning mirror (such as a MEMS mirror), a relay-system drive section (a projective optical system), and a see-through member arranged in front of the eyes (such as a holographic optical element (hereinafter referred to as a HOE in some cases)). Examples of the holographic optical element include a reflective or transmissive volume hologram and a reflective or transmissive relief hologram (also referred to as a surface relief hologram).

Figure 4:
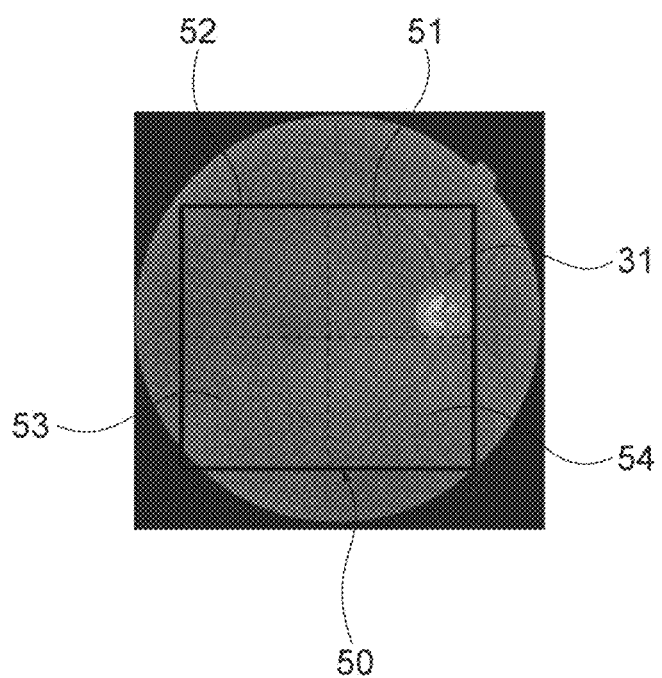
FIG. 4 is a diagram used to describe a result of matching performed on an interpolation eyeground map and a state of an eyeball to which a video is to be presented.

Steps S106 to 108 are specifically described with reference to FIG. 4. FIG. 4 is a diagram used to describe a result (a modification result) of matching performed on an interpolation eyeground map and a state of an eyeball to which a video is to be presented.

From among the first quadrant 51 (for example, a region in which an X axis is in a positive direction and a Y axis is in a positive direction), the second quadrant 52 (for example, a region in which the X axis is in a negative direction and the Y axis is in the positive direction), the third quadrant 53 (for example, a region in which the X axis is in the negative direction and the Y axis is in a negative direction), and the fourth quadrant 54 (for example, a region in which the X axis is in the positive direction and the Y axis is in the negative direction), the first to fourth quadrants 51 to 54 forming the video display range (angle of view) 50, the blind spot 31 is situated in the first quadrant 51 near the fourth quadrant 54, as illustrated in FIG. 4.

As indicated by reference numeral P1 in FIG. 1, Steps S106 to S108 are repeatedly performed until a desired or specified video is generated. Step S106 (gaze tracking) and Step S107 (generation of an interpolation eyeground map) may be performed at the same time.

Another example of the flow of displaying a video using the display apparatus of the first embodiment according to the present technology is described with reference to FIG. 5.

Figure 5:
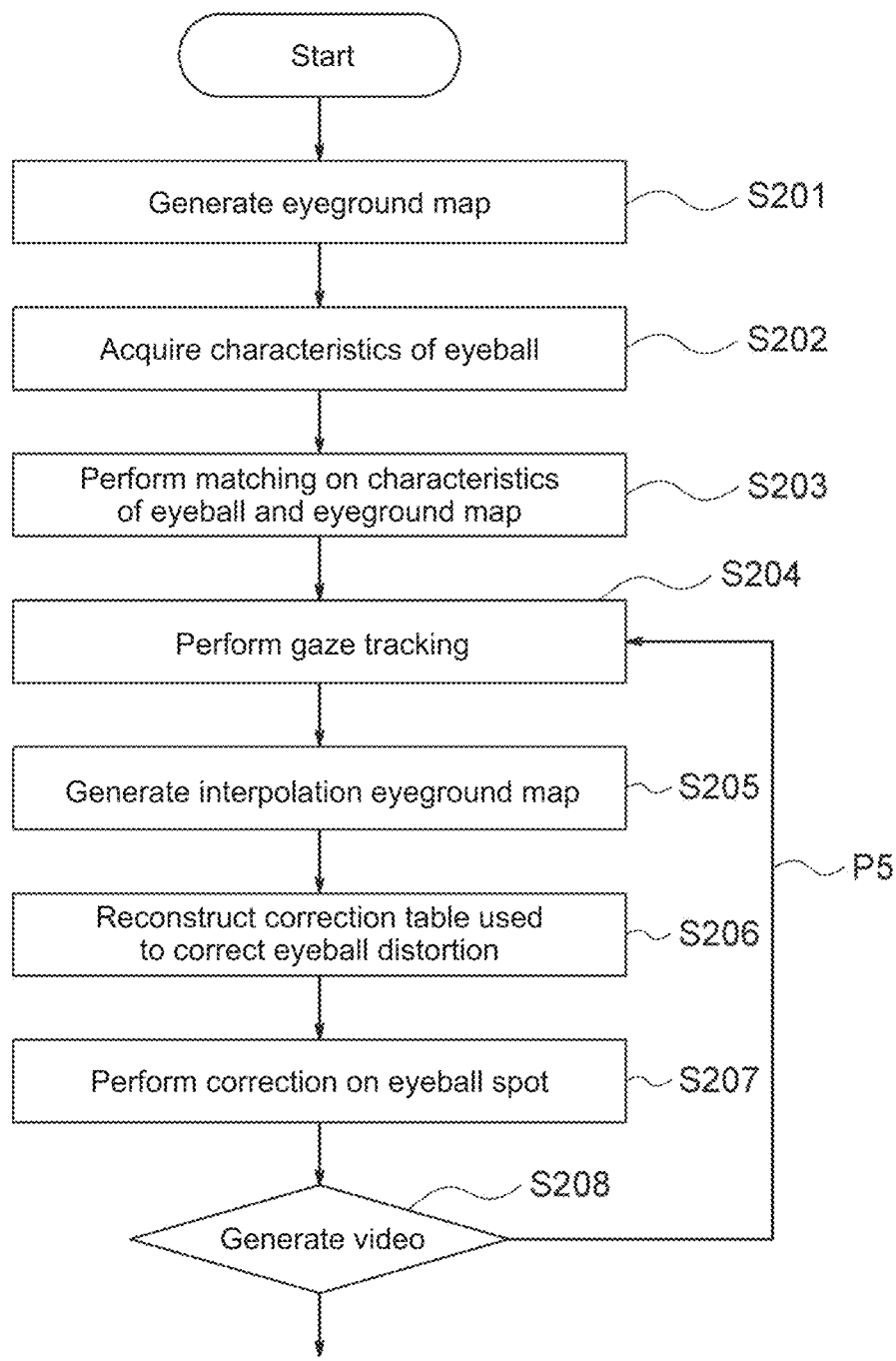
FIG. 5 illustrates another example of the flow of displaying a video using the display apparatus to which the present technology has been applied.

An eyeground map is generated in Step S201 illustrated in FIG. 5. A method for generating an eyeground map generated in Step S201 is similar to the method for generating an eyeground map generated in Steps S101 to S103 illustrated in FIG. 1. Thus, a detailed description is omitted here.

Figure 6:
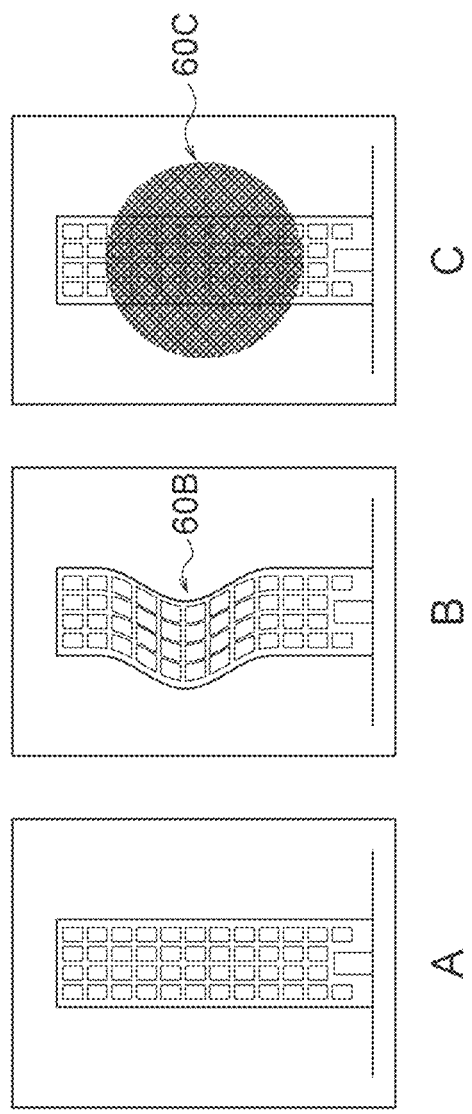
FIG. 6 is a diagram used to describe a state in which things can be seen normally, a state in which things appear distorted (metamorphopsia), and a state in which a center portion appears dark (central scotoma).

In Step S202 illustrated in FIG. 5, characteristics of an eyeball are acquired. The characteristics of an eyeball are acquired using, for example, an optical coherence tomography (OCT), a refractometer (objective refractometry), or a light detection apparatus that detects light that returns due to IR scanning. The use of an OCT makes it possible to capture an image of a cross section of a retina. The use of a refractometer makes it possible to obtain optical characteristics such as an aberration (such as data regarding eyeball distortion), and to measure, for example, a refractive power of an eye and a curvature of cornea. The use of a light detection apparatus that detects light that returns due to IR scanning makes it possible to measure, for example, a shape of an eyeground. The acquisition of characteristics of an eyeball makes it possible to determine, for example, whether an eye of a user is affected by age-related macular degeneration. The age-related macular degeneration is a disease that causes difficulty in seeing things by a macula that is a center portion of a retina being damaged due to a change with age or light damage. For example, as illustrated in FIG. 6, things can be seen normally with normal eyes (A of FIG. 6), whereas a retina becomes distorted due to age-related macular degeneration (metamorphopsia) and things appear distorted as in the case of, for example, a distortion 60B (B of FIG. 6), or an eyesight becomes weak due to age-related macular degeneration (metamorphopsia) and a center portion appears dark as in the case of, for example, a central scotoma 60C (C of FIG. 6).

Matching is performed on a result of eye sensing (eye tracking) and an eyeground map in Step S203 illustrated in FIG. 5. A matching method performed in Step S203 is similar to the matching method performed in Steps S104 and Step S105 illustrated in FIG. 1. Thus, a detailed description is omitted here.

Steps S204 to S208 illustrated in FIG. 5 are performed in a state in which a video is presented. In more detail, gaze tracking (line-of-sight tracking) is performed in Step S204. For example, in Step S204, a movement of an eyeball is followed, a position of a pupil is detected, and an angle of view of a desired point is calculated. Infrared light is caused to coincide with an optical axis used for image projection, and a fundus reflex (the reflectance at a position of a blind spot and the reflectance at a position of a fovea are different.) is detected. In Step S205, an interpolation eyeground map is generated. The interpolation eyeground map is generated by interpolating a leftward rotation, a rightward rotation, an upward rotation, and a downward rotation of an eyeball. For example, positions of a fovea and a blind spot when levels of a leftward rotation, a rightward rotation, an upward rotation, and a downward rotation of an eyeball are lower than levels of a leftward rotation, a rightward rotation, an upward rotation, and a downward rotation of the eyeball that are used for an eyeground map generated in Step S201 are estimated using the eyeground map to generate the interpolation eyeground map. Note that the interpolation eyeground map may be generated using information regarding a position of a specific eyeball, or information regarding a shift of an angle of view.

Figure 7:
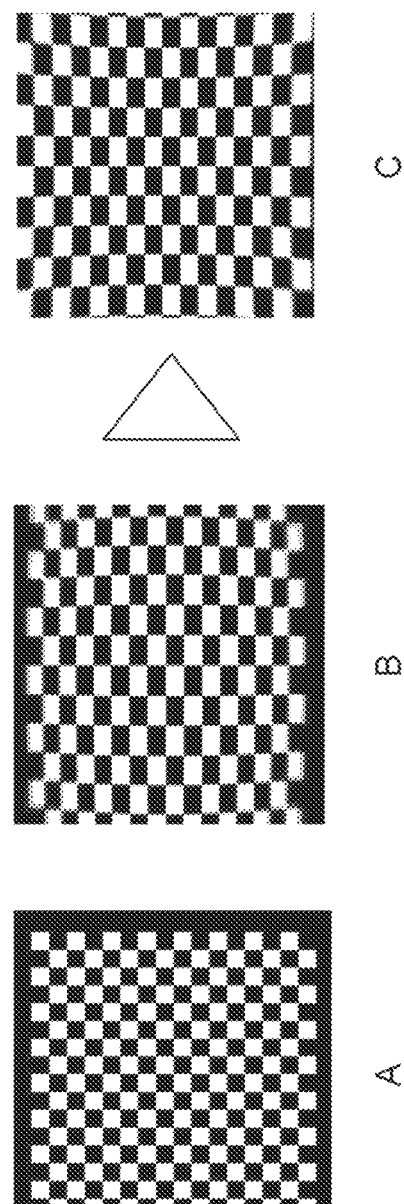
FIG. 7 is a diagram used to describe correction performed on an eyeball distortion.

Next, a correction table used to correct an eyeball distortion is reconstructed in Step S206. Step S206 is specifically described with reference to FIG. 7. A of FIG. 7 illustrates a video (an image) to be presented. B of FIG. 7 illustrates the video (the image) affected by an eyeball distortion. C of FIG. 7 illustrates an output video (a generated video) obtained by correction being performed using a correction table used to correct an eyeball distortion.

Figure 8:
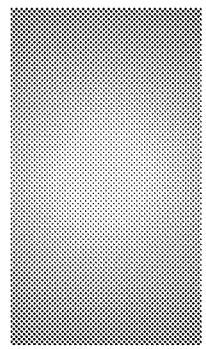
FIG. 8 is a diagram used to describe correction performed on an eyeball spot.
Figure 8:
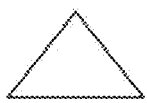
Figure 8:
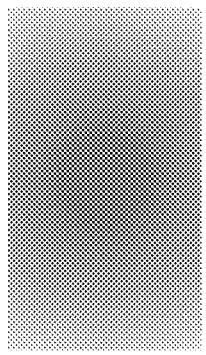
Figure 8:
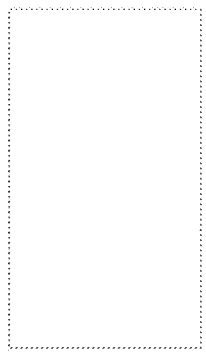

Correction is performed on an eyeball spot in Step S207. Step S207 is specifically described with reference to FIG. 8. A of FIG. 8 illustrates a video (an image) to be presented. B of FIG. 8 illustrates the video (the image) affected by an eyeball spot. C of FIG. 8 illustrates an output video (a generated video) obtained by correction performed by the eyeball-spot correction.

Then, a video is generated in Step S208. After the video is generated, a signal of the generated video is transmitted to a video display section that includes, for example, a light source (such as a laser source), a mirror, a scanning mirror (such as a MEMS mirror), a relay-system drive section (a projective optical system), and a see-through member (such as a holographic optical element (hereinafter referred to as an HOE in some cases)). Examples of the holographic optical element include a reflective or transmissive volume hologram and a reflective or transmissive relief hologram (also referred to as a surface relief hologram).

As indicated by reference numeral P5 in FIG. 5, Steps S204 to S208 are repeatedly performed until a desired or specified video is generated. Step S204 (gaze tracking) and Step S205 (generation of an interpolation eyeground map) may be performed at the same time.

Figure 9:
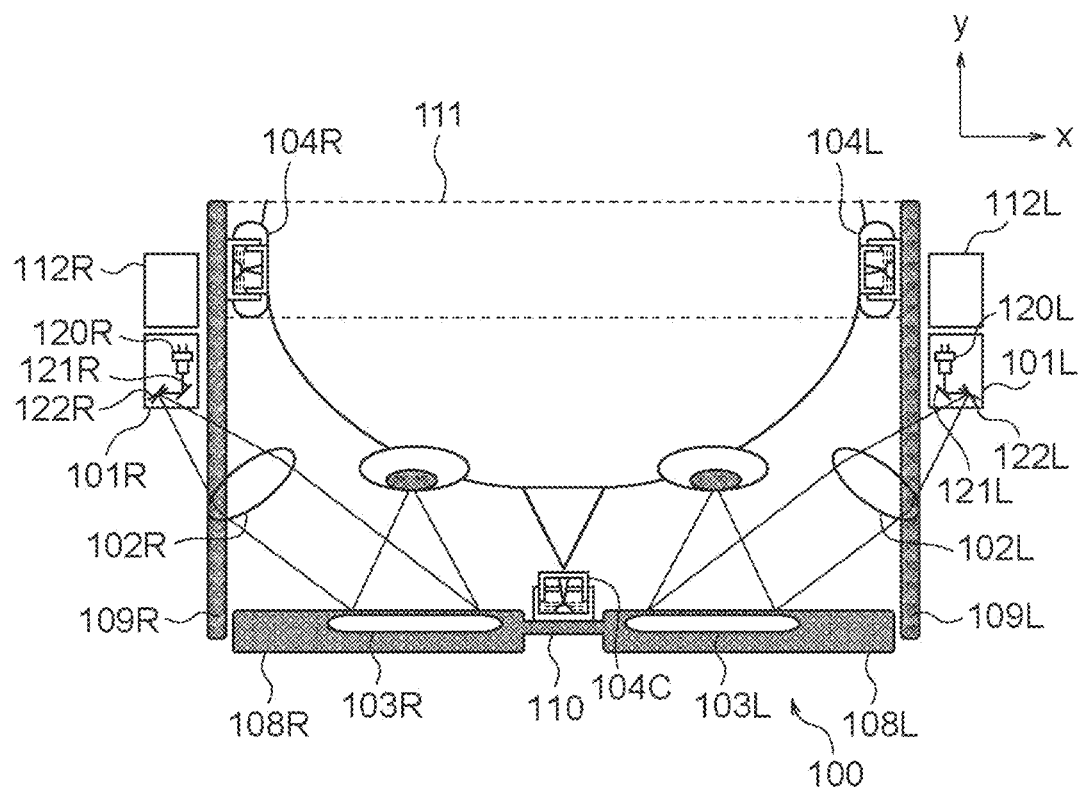
FIG. 9 is a top view illustrating an example of a configuration of a display apparatus to which the present technology has been applied.
Figure 10:
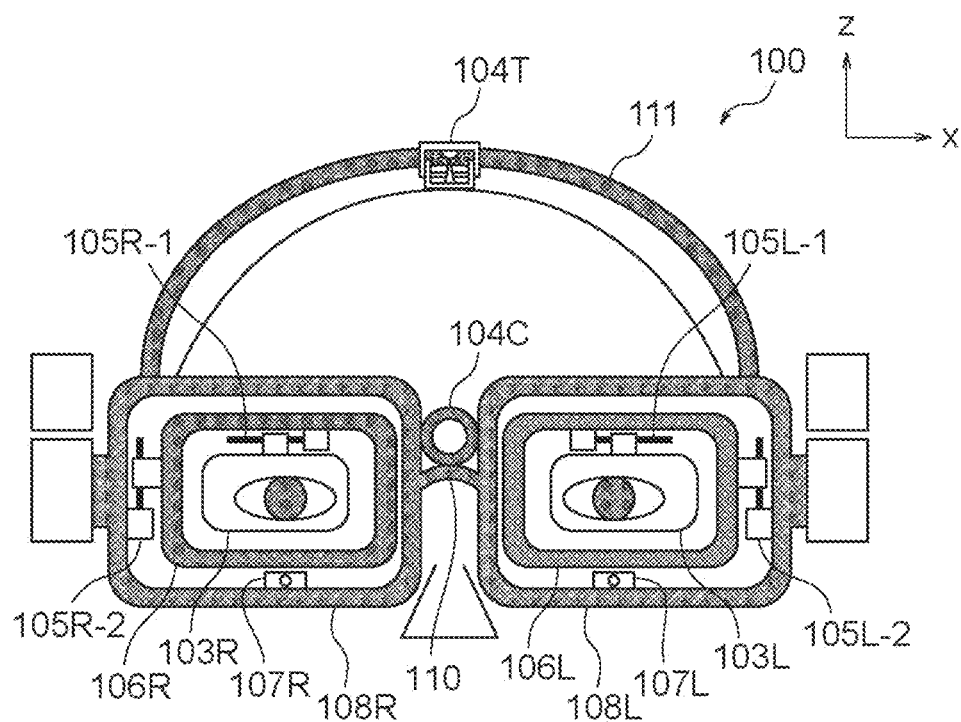
FIG. 10 is a front view illustrating the example of the configuration of the display apparatus to which the present technology has been applied.

An example of a configuration of the display apparatus of the first embodiment according to the present technology is described with reference to FIGS. 9 and 10. FIG. 9 is a top view of a display apparatus according to the present technology that is worn on the head of a user. FIG. 10 is a front view of the display apparatus according to the present technology being worn on the head of the user. The display apparatus illustrated in FIG. 9 includes a video display section (also referred to as an image display section), a sensor that detects a change in a position of the display apparatus relative to the head (the sensor detecting a change in a position of the display apparatus relative to the head is herein also referred to as a "displacement sensor" or a "sensor"), a monitoring section, a projection position adjusting mechanism, a controller, and a storage. Those structural elements are described below.

(Video Display Section)

As illustrated in FIG. 9, a display apparatus 100 has a shape of glasses, and is configured to project video display light (referred to as image display light in some cases) onto each of the eyes. In other words, the display apparatus 100 includes a video display section that projects video display light onto the left eye, and a video display section that projects video display light onto the right eye. The video display section projecting video display light onto the left eye includes a light source section 101L, a projective optical system 102L, and a holographic optical element (hereinafter also referred to as an HOE) 103L that serves as an irradiator. The display apparatus 100 may include a combiner that serves as a follower, and the combiner may structurally include, for example, the holographic optical element 103L and a half mirror, although this is not illustrated. The projective optical system 102L may include a relay-system drive section (not illustrated) that servers as a follower. A mirror drive section and a phase difference panel that serve as a follower may be arranged between the light source section 101L and the projective optical system 102L, or between the projective optical system 102L and the holographic optical element 103L.

The light source section 101L emits video display light. The light source section 101L may include, for example, a laser source 120L, a mirror 121L, and a scanning mirror 122L that are structural elements used to emit the video display light. Laser light emitted by the laser source 120L is reflected off the mirror 121L, and then reaches the scanning mirror 122L. The scanning mirror 122L two-dimensionally scans the laser light. The scanning mirror 122L may be, for example, a MEMS mirror. The scanning mirror 122L may move a direction of the laser light quickly such that an image is formed on a retina.

The projective optical system 102L adjusts the direction of the video display light such that the video display light reaches a desired region and/or position in the HOE 103L. For example, the projective optical system 102L forms the video display light scanned by the scanning mirror 122L into parallel light.

The HOE 103L diffracts the video display light such that the video display light is concentrated at a position near a pupil of a user to be irradiated onto a retina. The HOE 103L may be, for example, a reflective diffractive element. The HOE 103L may have the optical characteristics of serving as a lens with respect to light in a range of a wavelength of the video display light, and of causing light of a wavelength outside of the wavelength range to be transmitted through the HOE 103L. The optical characteristics enable a user to recognize, for example, the scenery ahead of a line of sight through the HOE 103L, and to recognize an image made up of the video display light. In other words, an image made up of the video display light can be superimposed on the scenery in the outside world. Examples of the HOE 103L include a hologram lens, favorably include a hologram lens in the form of a film, and more favorably include a transparent hologram lens in the form of a film. The hologram lens in the form of a film may be used by being attached to, for example, glass. An existing approach in this technical field makes it possible to give desired optical characteristics to the hologram lens. Further, the HOE 103L may be, for example, a volume hologram or a surface relief hologram. Further, a commercially available hologram lens may be used as the hologram lens, or the hologram lens may be produced using the existing approach in this technical field.

As described above, the light source section 101L, the projective optical system 102L, and the HOE 103L cause video display light to reach the left eye of the user.

The display apparatus 100 includes a temple 109L and a rim 108L that are a portion of the shape of glasses. The light source section 101L and the projective optical system 102L are arranged in the temple 109L. The HOE 103L is held in the rim 108L. More specifically, an inner rim 106L is held in the rim 108L through a projection position adjusting mechanism 105L-2 that serves as an irradiator, and the HOE 103L is held in the inner rim 106L through a projection position adjusting mechanism 105L-1 that serves as an irradiator.

The video display section projecting video display light onto the right eye of the user includes a light source section 101R, a projective optical system 102R, and an HOE 103R that serves as an irradiator. The display apparatus 100 may include a combiner that serves as a follower, and the combiner may structurally include, for example, the HOE 103R and a half mirror, although this is not illustrated. The projective optical system 102R may include a relay-system drive section (not illustrated) that servers as a follower. A mirror drive section and a phase difference panel that serve as a follower may be arranged between the light source section 101R and the projective optical system 102R, or between the projective optical system 102R and the HOE 103R.

With respect to the descriptions of the light source section 101L, the projective optical system 102L, and the HOE 103L, the same applies to the light source section 101R, the projective optical system 102R, and the HOE 103R.

As in the case of the left-eye video display section, the light source section 101R and the projective optical system 102R are arranged in a temple 109R. The HOE 103R is held in a rim 108R. More specifically, an inner rim 106R is held in the rim 108R through a projection position adjusting mechanism 105R-2 that serves as an irradiator, and the HOE 103R is held in the inner rim 106R through a projection position adjusting mechanism 105R-1 that serves as an irradiator.

The rims 108L and 108R of the display apparatus 100 are connected to each other through a bridge 110. The bridge 110 is a portion that spans the nose of a user when the user is wearing the display apparatus 100. Further, both of the rims 108L and 108R of the display apparatus 100 are connected to a headband 111. The headband 111 is a portion that is brought into contact with the top of the head of a user, as illustrated in FIG. 10, when the user is wearing the display apparatus 100.

The light source section 101L illustrated in FIG. 9 includes one laser source 120L. However, the number of laser sources included in the light source section 101L may be two or more, and may be, for example, from two to five. The laser sources of a plurality of the laser sources may output pieces of laser light of wavelengths different from each other. Likewise, the light source section 101R includes one laser source 120R. However, the number of laser sources included in the light source section 101R may be two or more, and may be, for example, from two to five. The laser sources of a plurality of the laser sources may output pieces of laser light of wavelengths different from each other. The use of the laser source 120L and the laser source 120R makes it possible to present a stimulus of a specific wavelength.

The display apparatus 100 may further include a member for compensating for a wavelength dispersion, although this is not illustrated. Examples of the member for compensating for a wavelength dispersion include the first optical element including a reflective or transmissive volume hologram, a reflective or transmissive relief hologram, or a meta-surface. The member for compensating for a wavelength dispersion may be arranged around the mirror 121L and/or 121R such as between the mirror 121L and the scanning mirror 122L, and/or between the mirror 121R and the scanning mirror 122R. The application of a member for compensating for a wavelength dispersion to the display apparatus 100 causes a wavelength dispersion to be compensated for, and thus makes it possible to precisely stimulate any point (a specified point) on a retina.

(Sensor)

The display apparatus 100 further includes sensors 104L, 104R, 104C, and 104T that detect a change in the position of the display apparatus 100 relative to the head of a user. The positional change detected by the sensors may be, for example, a direction of the positional change and/or an amount of the positional change. Note that the sensors 104L, 104R, 104C, and 104T may be herein collectively referred to as sensors 104.

The sensors 104L and 104R detect a horizontal change in the position of the display apparatus 100 relative to the head of a user, the sensor 104C detects a change in the position of the display apparatus 100 relative to the head of the user in a back-and-forth direction, and the sensor 104T detects a change in the position of the display apparatus 100 relative to the head of the user in an up-and-down direction. This makes it possible to three-dimensionally grasp a state of being worn with an offset.

(Monitoring Section (Line-of-Sight Detecting Apparatus))

The display apparatus 100 includes monitoring sections 107L and 107R that detect a line of sight of a user. The monitoring sections 107L and 107R may be herein collectively referred to as monitoring sections 107. The monitoring section 107 can monitor a state of the eyeball using a corneal reflex or a fundus reflex. The display apparatus 100 includes the monitoring sections, and this makes it possible to adjust the position of an image presented to a user such that the image is presented at a more appropriate position. For example, when an image presented by the display apparatus 100 is superimposed on an image of the outside world, the superimposed image can be displayed at a more appropriate position by detecting a line of sight of a user. In other words, the inclusion of the monitoring section 107 is favorable for presentation of AR information. The monitoring section may be, for example, a line-of-sight detecting apparatus.

The monitoring section 107 may be, for example, an imaging-type monitoring section or a photodiode-type monitoring section. Those monitoring sections are described below in more detail.

The monitoring section 107L detects a line of sight of a left eye of a user. The monitoring section 107L may be provided to, for example, any location in the rim 108L, and may be provided to any location in another component (such as the inner rim 106L) as long as the monitoring section 107L can detect the line of sight of the left eye.

The monitoring section 107L may be, for example, a photodiode-type monitoring section. The photodiode-type monitoring section may include, for example, a combination of a light source and a photodiode. The light source is configured to irradiate light onto a left eye. The light source is favorably an infrared light illuminating light source. This makes it possible to prevent recognition of an image in the outside world and recognition of video display light that are performed by a user from being affected. The photodiode may be configured to detect light (specifically, infrared light) that is emitted by the light source and reflected off an eyeball. For example, the photodiode may be capable of detecting a difference between an amount of light reflected off a non-white part of an eyeball (pupil) and an amount of light reflected off a white part of the eyeball (sclera). For example, the photodiode-type monitoring section may detect a line of sight on the basis of a proportion of the area of a non-white part of an eyeball and a proportion of the area of a white part of the eyeball, the area proportions being detected by the photodiode.

The photodiode-type monitoring section does not detect a state of being worn with an offset when the display apparatus is in the state of being worn with an offset. Thus, when the display apparatus is in the state of being worn with an offset, there may be a reduction in the accuracy in detection of a line of sight that is performed by the monitoring section. As described above, the display apparatus of the present technology includes a sensor that detects a change in the position of the display apparatus relative to the head, and this makes it possible to detect a state of being worn with an offset. A line of sight is corrected on the basis of a state of being worn with an offset that is detected by the sensor, and this results in improving the accuracy in detection of a line of sight that is performed by the monitoring section. The display apparatus of the present technology may detect a line of sight with the accuracy of, for example, 3 mm or less, specifically with the accuracy of 2 mm or less, and more specifically, with the accuracy of 1 mm or less. The detection of a line of sight with such accuracy is particularly favorable for a Maxwellian viewing presentation of an image.

Alternatively, the monitoring section 107L may be an imaging-type monitoring section. The imaging-type monitoring section may include, for example, a combination of a light source and an imaging device. As in the case of the photodiode-type monitoring section, the light source is configured to irradiate light onto a left eye. The light source is favorably an infrared light illuminating light source. For example, the imaging device may be capable of obtaining a reflection image (a so-called Purkinje image) obtained by light from the light source being reflected off an eyeball (specifically, a cornea), and an image from which the center of gravity of a pupil can be acquired. The imaging device may be, for example, an infrared imaging device. For example, the imaging-type monitoring section may estimate an optical axis of an eyeball on the basis of the Purkinje image and the image described above. The monitoring section may convert the estimated optical axis into a visual axis to detect a line of sight.

The position at which the Purkinje image is formed will be fixed when a positional relationship between the light source and an eyeball remains unchanged upon detecting a line of sight on the basis of the Purkinje image and the image described above. The state of being worn with an offset results in a change in the positional relationship. This may result in changing the position at which the Purkinje image is formed. In addition, the line-of-sight detection is easily affected by, for example, a blink, the hair of head, or eyelashes. Further, in the line-of-sight detection, calibration is usually performed to correct for an individual difference, and there is a need to perform calibration again when the display apparatus is in the state of being worn with an offset. As described above, the display apparatus of the present technology includes a sensor that detects a change in the position of the display apparatus relative to the head, and this makes it possible to detect a state of being worn with an offset. Thus, a correction value corresponding to, for example, an amount of being worn with an offset is provided in advance (by, for example, being stored in a storage), and correction is performed using the correction value in response to the display apparatus being worn with an offset. This makes it possible to accurately detect a line of sight. In addition, the detection of a state of being worn with an offset is less likely to be affected by, for example, a blink, the hair of head, or eyelashes. Further, the correction based on the detected state of being worn with an offset also makes it possible to reduce the number of times that calibration is performed.

(Projection Position Adjusting Mechanism)

An irradiator included in the display apparatus 100 may further include the projection position adjusting mechanisms 105L-1, 105L-2, 105R-1, and 105R-2 adjusting a projection position of video display light that is emitted from the display apparatus 100. Note that the four projection position adjusting mechanisms may be herein collectively referred to as projection position adjusting mechanisms 105. For example, the projection position adjusting mechanism 105 may be configured to adjust the projection position of video display light such that the video display light follows a line of sight. The projection position adjusting mechanism 105 makes it possible to adjust the projection position of video display light according to a state of being worn with an offset.

In addition, the projection position adjusting mechanisms 105 make it possible to adjust a projection position of video display light according to a rotational movement of an eyeball or a movement of a line of sight. For example, the display apparatus 100 includes the projection position adjusting mechanisms 105, and this makes it possible to adjust the position of an image presented to a user such that the image is presented at a more appropriate position. For example, when an image presented by the display apparatus 100 is superimposed on an image of the outside world, the superimposed image can be displayed at a more appropriate position by detecting a line of sight of a user. In other words, the inclusion of the monitoring section 107 is favorable for presentation of AR information. Further, the projection position adjusting mechanisms also make it possible to adjust a position at which video display light is concentrated upon Maxwellian viewing presentation of an image.

The projection position adjusting mechanisms 105L-1 and 105L-2 adjust a projection position of video display light projected onto a left eye. The projection position adjusting mechanism 105L-1 adjusts a positional relationship between the inner rim 106L and the rim 108L in a z-axis direction. For example, the projection position adjusting mechanism 105L-1 moves the inner rim 106L in the z-axis direction relative to the rim 108L. This results in adjusting a position of the HOE 103L in the z-axis direction. The projection position adjusting mechanism 105L-2 adjusts a positional relationship between the HOE 103L and the inner rim 106L in an x-axis direction. For example, the projection position adjusting mechanism 105L-2 moves the HOE 103L in the x-axis direction relative to the inner rim 106L. This results in adjusting the position of the HOE 103L in the x-axis direction.

A drive element used to drive adjustment of the positional relationship between the inner rim 106L and the rim 108L in the z-axis direction that is performed by the projection position adjusting mechanism 105L-1 may be, for example, a piezo element, an actuator, or bimetal, but is not limited thereto. Likewise, a drive element used to drive adjustment of the positional relationship between the HOE 103L and the inner rim 106L in the x-axis direction that is performed by the projection position adjusting mechanism 105L-2 may be, for example, a piezo element, an actuator, or bimetal, but is not limited thereto.

For example, the projection position adjusting mechanism 105L-1 may adjust a positional relationship between the inner rim 106L and the rim 108L in the z-axis direction on the basis of a change in the position of the display apparatus 100 that is detected by one of, two of, three of, or all of four of the sensors 104L, 104R, 104C, and 104T. Further, the projection position adjusting mechanism 105L-1 may adjust the positional relationship on the basis of the positional change and a line of sight detected by the monitoring section 107L. For example, the projection position adjusting mechanism 105L-2 may adjust a positional relationship between the HOE 103L and the inner rim 106L in the x-axis direction on the basis of a change in the position of the display apparatus 100 that is detected by one of, two of, three of, or all of four of the sensors 104L, 104R, 104C, and 104T. Further, the projection position adjusting mechanism 105L-2 may adjust the positional relationship on the basis of the positional change and a line of sight detected by the monitoring section 107L.

The projection position adjusting mechanisms 105R-1 and 105R-2 adjust a projection position of video display light projected onto a right eye. The adjustment may be performed similarly to the adjustment performed by the projection position adjusting mechanisms 105L-1 and 105L-2.

(Controller and Storage)

Figure 11:
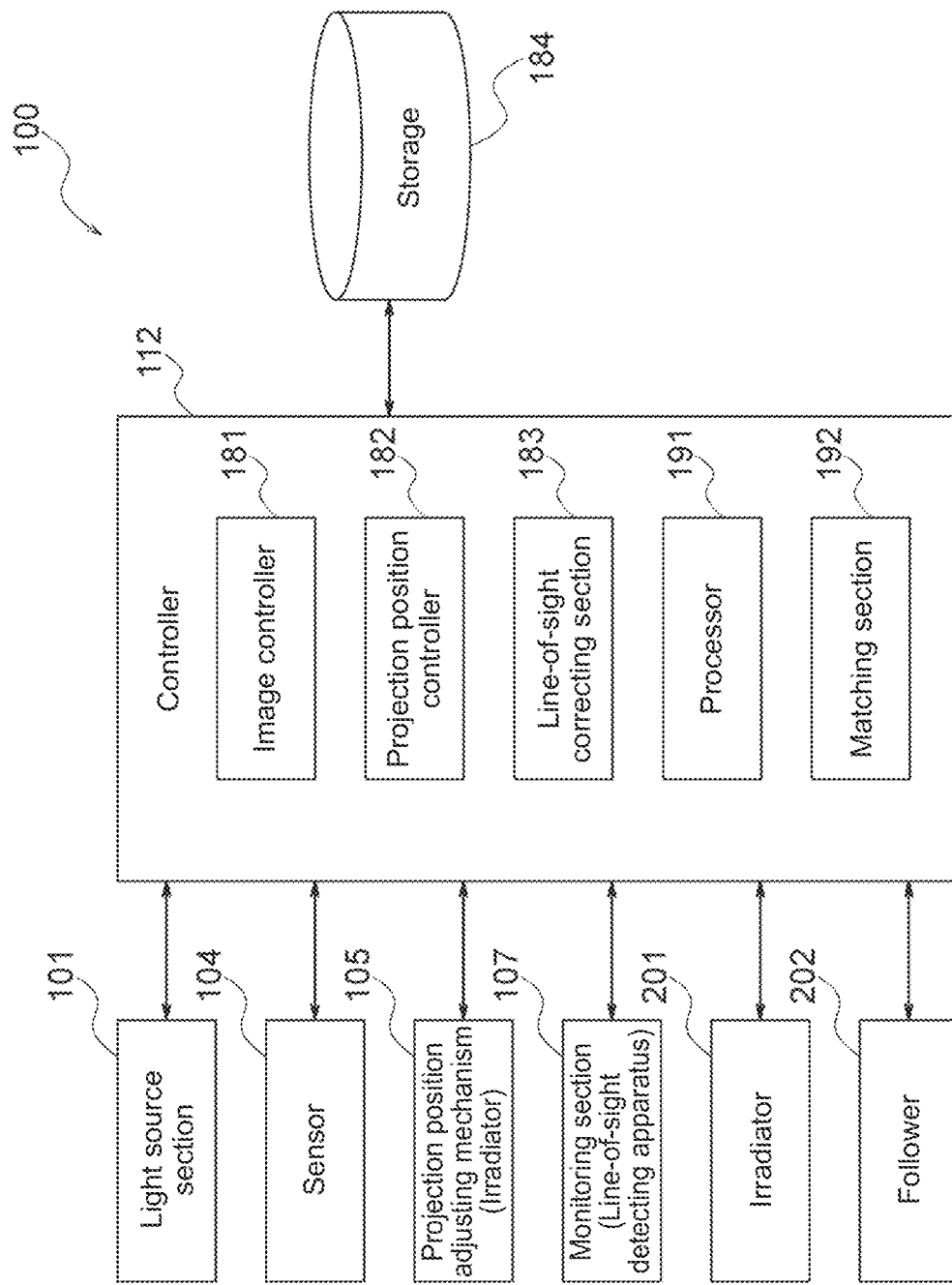
FIG. 11 is a block diagram illustrating an example of a configuration of a display apparatus of a first embodiment to which the present technology has been applied.

The display apparatus 100 includes a controller 112. As illustrated in FIG. 11, which is a block diagram illustrating primary structural elements of the display apparatus 100, the controller 112 includes an image controller 181, a projection position controller 182, a line-of-sight correcting section 183, a processor 191, and a matching section 192. Further, as described above, the display apparatus 100 illustrated in FIG. 11 includes a light source section 101, the sensor 104, the projection position adjusting mechanism 105 serving as an irradiator, the monitoring section (a line-of-sight detecting mechanism) 107, an irradiator 201 that includes a see-through member arranged in front of the eyes (such as a reflective or transmissive volume hologram or a reflective or transmissive relief hologram), and a follower 202. Note that the display apparatus 100 does not necessarily have to include the follower 202. A storage 184 may be included in the display apparatus 100, or may be included in an external apparatus other than the display apparatus 100.

Figure 13:
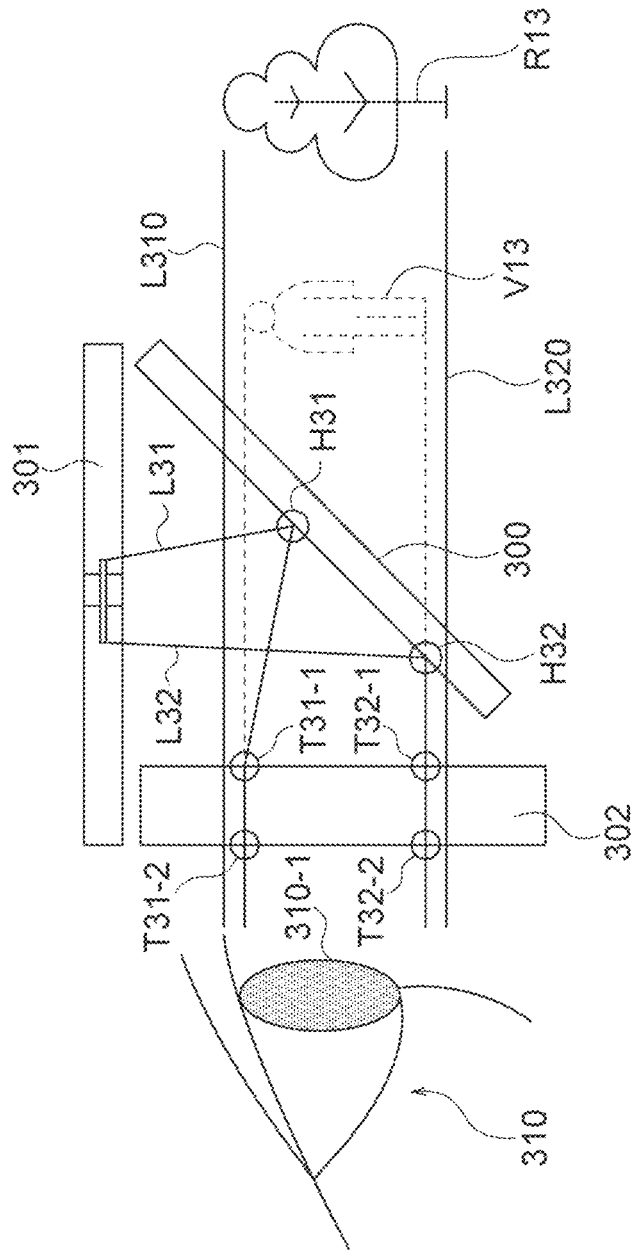
FIG. 13 illustrates an example of a member that is arranged in front of the eyes and included in the display apparatus to which the present technology has been applied.
Figure 14:
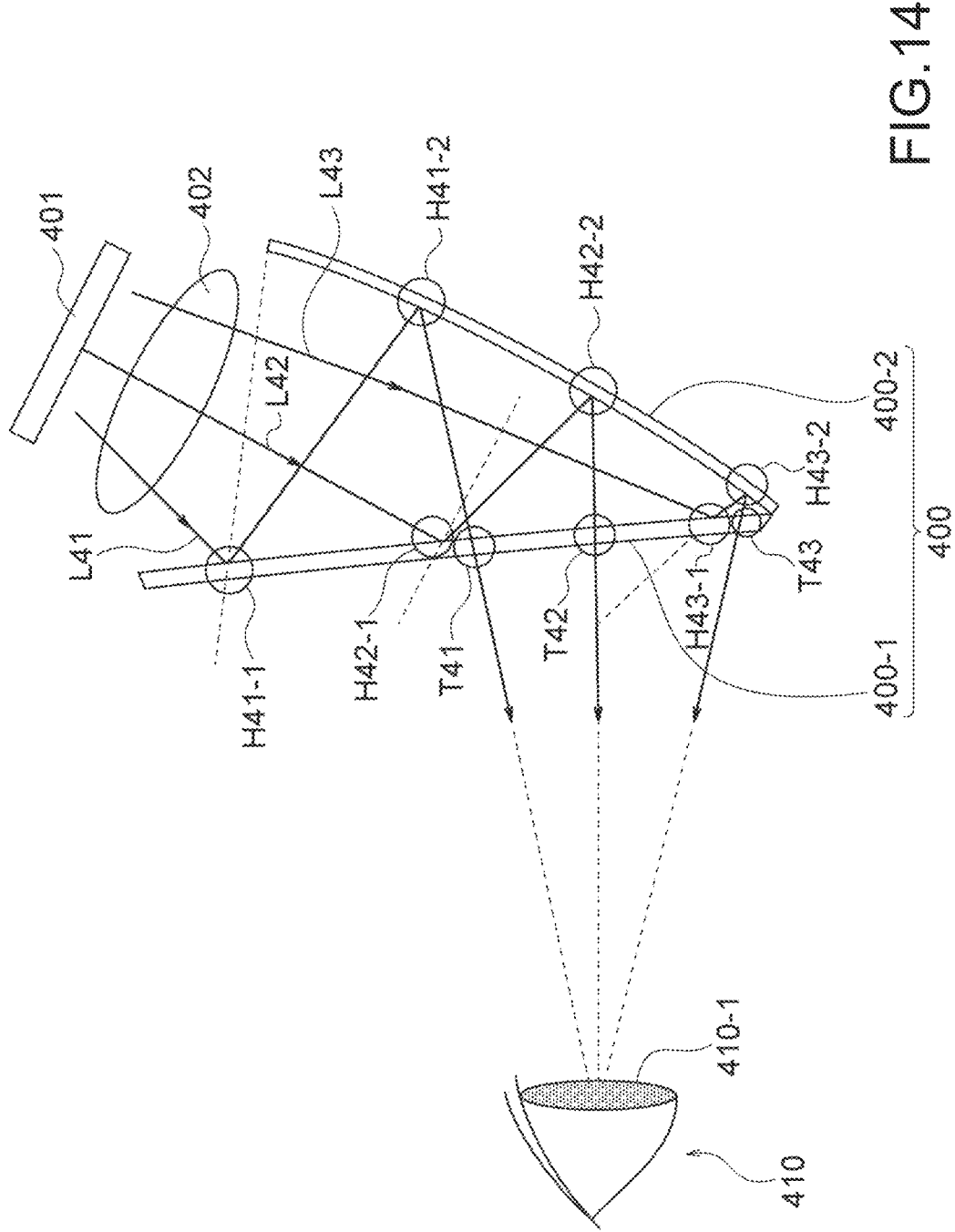
FIG. 14 illustrates another example of the member being arranged in front of the eyes and included in the display apparatus to which the present technology has been applied.

The member being arranged in front of the eyes and included in the irradiator 201 of the display apparatus 100 has been described above, and examples of using the members arranged in front of the eyes of FIGS. 13 and 14 are described in more detail.

FIG. 13 illustrates a second optical element 300 that is an example of the member arranged in front of the eyes, where specified light is reflected off the second optical element 300 and light other than the specified light is transmitted through the second optical element 300. FIG. 14 illustrates a second optical element 400 that is another example of the member arranged in front of the eyes, where specified light is reflected off the second optical element 400 and light other than the specified light is transmitted through the second optical element 400.

An apparatus illustrated in FIG. 13 includes the second optical element 300, a liquid crystal panel 301, and the special liquid crystal lens 302. The second optical element 300 includes a polarizing beam splitter (PBS), and a λ/4 plate is arranged in the second optical element (polarizing beam splitter) 300 although this is not illustrated. The apparatus illustrated in FIG. 13 does not necessarily have to include the special liquid crystal lens 302, and, instead of the special liquid crystal lens 302, the apparatus illustrated in FIG. 13 may include a lens between the liquid crystal panel 301 and the second optical element 300.

As illustrated in FIG. 13, a ray of polarized light (video display light) L31 from the liquid crystal panel 310 is reflected off a region H31 in the second optical element 300, and is transmitted through regions T31-1 and T31-2 in the special liquid crystal lens 302 to reach an eye 310 (a pupil 310-1) of a user. A ray of polarized light (video display light) L32 from the liquid crystal panel 301 is reflected off a region H32 in the second optical element 300 (polarizing beam splitter), and is transmitted through regions T32-1 and T32-2 in the special liquid crystal lens 302 to reach the eye 310 (the pupil 310-1) of the user. The user recognizes a virtual video (image) V13 made up of light (video display light (the rays of polarized light L31 and L32)) emitted by the liquid crystal panel 301. Then, pieces of light L310 and L320 from the outside world are transmitted through the second optical element 300 (polarizing beam splitter), and are transmitted through the special liquid crystal lens 302 to reach the eye 310 (the pupil 310-1) of the user. The user recognizes a reality video (image) R13 made up of the pieces of light L310 and L320 from the outside world. In other words, the user recognizes as if (it looks to the user like) the virtual video (image) V13 is superimposed on the reality video (image) R13.

FIG. 14 illustrates the second optical element 400, an organic light emitting diode (OLED) panel (organic EL) 401, and a lens 402. The second optical element 400 is an aspheric half mirror, and includes a first mirror member 400-1 and a second mirror member 400-2. For example, the second optical element 400 may include a half mirror 400-1 and a half mirror 400-2 in combination, or may include a polarizing beam splitter (PBS) 400-1 and the half mirror 400-2 in combination. When the second optical element 400 includes the polarizing beam splitter (PBS) 400-1 and the half mirror 400-2 in combination, a λ/4 plate may be arranged in the half mirror 400-2. When the first mirror member 400-1 or the second mirror member 400-2 is a half mirror, or when both the first mirror member 400-1 and the second mirror member 400-2 are half mirrors, the light transmittance is favorably 50% or more.

As illustrated in FIG. 14, a light ray (video display light) L41 from the organic light emitting diode (OLEO) panel (organic EL) 401 is reflected off a region H41-1 in the first mirror member 400-1 included in the second optical element 400. Subsequently, the light ray L41 is reflected off a region H41-2 in the second mirror member 400-2 included in the second optical element 400, and is transmitted through a region T41 in the first mirror member 400-1 to reach an eye 410 (a pupil 410-1) of a user. A light ray (video display light) L42 from the OLEO panel 401 is reflected off a region H42-1 in the first mirror member 400-1 included in the second optical element 400. Subsequently, the light ray L42 is reflected off a region H42-2 in the second mirror member 400-2 included in the second optical element 400, and is transmitted through a region T42 in the first mirror member 400-1 to reach the eye 410 (the pupil 410-1) of the user. A light ray (video display light) L43 from the OLEO panel 401 is reflected off a region H43-1 in the first mirror member 400-1 included in the second optical element 400. Subsequently, the light ray L43 is reflected off a region H43-2 in the second mirror member 400-2 included in the second optical element 400, and is transmitted through a region T43 in the first mirror member 400-1 to reach the eye 410 (the pupil 410-1) of the user. The user recognizes a virtual video (image) made up of light (video display light (the light rays L41, L42, and L43)) emitted by the OLED panel 401. Then, light from the outside world is transmitted through the second optical element 400 to reach the eye 410 (the pupil 410-1) of the user, although this is not illustrated. The user recognizes a reality video (image) made up of the light from the outside world. The user recognizes as if the virtual video (image) is superimposed on the reality video (image).

Note that contents related to the two examples of the member being arranged in front of the eyes and included in the irradiator 201 have been described above with reference to FIGS. 13 and 14. The contents may also be applied to a display apparatus 100-1 of a second embodiment according to the present technology. This will be described later.

The controller 112 is described below.

The image controller 181 controls projection of video display light that is performed by the video display section. For example, the image controller 181 drives the light source sections 101L and 101R, that is, the image controller 181 drives in particular the laser sources and scanning mirrors included in these light source sections, and causes the light source sections to output pieces of video display light. For example, the image controller 181 may acquire image data stored in the storage 184, and may cause the light source sections 101L and 101R to output pieces of video display light on the basis of the acquired image data. The image controller 181 may correct the image data on the basis of a change in the position of the display apparatus 100 relative to the head of a user, the change being detected by the sensor 104. On the basis of the image data after the correction, the image controller 181 may cause the light source sections 101L and 101R to output pieces of video display light. In other words, the display apparatus 100 may correct an image on the basis of a change in the position of the display apparatus relative to the head of a user, the positional change being detected by a sensor that detects the positional change.

The projection position controller 182 controls the projection position adjusting mechanisms 105L-1, 105L-2, 105R-1, and 105R-2, and this results in being able to control a projection position of video display light. For example, the projection position controller 182 may adjust the projection position of video display light by driving one of, two of, three of, or four of the projection position adjusting mechanisms 105L-1, 105L-2, 105R-1, and 105R-2 on the basis of a line of sight detected by the monitoring sections 107L and 107R. For example, the projection position of video display light may be adjusted such that the video display light follows the line of sight. The projection position controller 182 may adjust the projection position of video display light by driving one of, two of, three of, or four of the projection position adjusting mechanisms 105L-1, 105L-2, 105R-1, and 105R-2 on the basis of the line of sight after correction performed by the line-of-sight correcting section 183, which will be described later. For example, the projection position of video display light may be adjusted such that the video display light follows the line of sight after the correction. The projection position controller 182 may adjust the projection position of video display light by driving one of, two of, three of, or four of the projection position adjusting mechanisms 105L-1, 105L-2, 105R-1, and 105R-2 on the basis of data (hereinafter also referred to as "displacement data") related to a change in the position of the display apparatus 100 relative to the head of a user, the change being detected by one of, two of, three of, or four of the sensors 104L, 104R, 104C, and 104T.

For example, the projection position controller 182 may calculate an amount of positional adjustment performed by each projection position adjusting mechanism on the basis of the displacement data and a correction coefficient. The projection position controller 182 may drive each projection position adjusting mechanism such that a positional relationship is changed by the calculated amount of positional adjustment. For example, the projection position controller 182 may acquire a correction coefficient from a correction table stored in the storage 184 in advance, and may use the acquired correction coefficient in order to calculate the amount of positional adjustment. For example, the correction table may include a plurality of correction coefficients, and the projection position controller 182 may select a specified correction coefficient from the plurality of correction coefficients according to the displacement data. Further, for example, the correction table may be provided for each projection position adjusting mechanism. The correction table may be included in the display apparatus 100 in advance, or may be updated in response to the display apparatus 100 being used by a user. The selection or the update of a correction table or a correction coefficient makes it possible to improve the accuracy in controlling a projection position. In order to calculate the amount of positional adjustment, the projection position controller 182 may use a line of sight detected by the monitoring section, or a line of sight after correction performed by the line-of-sight correcting section 183.

The line-of-sight correcting section 183 corrects a line of sight detected by the monitoring sections 107L and 107R, on the basis of the displacement data. This enables the line-of-sight correcting section 183 to identify a line of sight in consideration of a state of being worn with an offset, and this results in improving the accuracy in detecting a line of sight. The correction may be performed with respect to an optical axis of an eyeball, may be performed with respect to a visual axis of the eyeball, or may be performed with respect to a reference axis other than the optical axis and the visual axis. Likewise, the line-of-sight correcting section 183 may acquire a correction coefficient from a correction table stored in the storage 184 in advance, and may use the acquired correction coefficient in order to correct a line of sight. For example, the correction table may include a plurality of correction coefficients, and the line-of-sight correcting section 183 may select a specified correction coefficient from the plurality of correction coefficients according to the displacement data. The correction table may be included in the display apparatus 100 in advance, or may be updated in response to the head-mounted display apparatus 100 being used by a user. The selection or the update of a correction table or a correction coefficient makes it possible to improve the accuracy in correcting a line of sight.

The display apparatus 100 may further include the storage 184. The storage may store therein data related to video display light projected by the video display section, a correction table used by the projection position controller 122 to control a projection position, and a correction table used by the line-of-sight correcting section 123 to correct a line of sight.

The processor 191 performs processing on information regarding a distribution of characteristics of an eyeball. For example, the distribution of characteristics of an eyeball is acquired using a fundus camera, or is acquired using an OCT, a refractometer, or a light detection apparatus that detects light that returns due to IR scanning. The distribution of characteristics of an eyeball may be acquired from shape characteristics (such as a size and a shape of an eyeball, a size and a shape of a macula (such as a form of a recess), a size and a shape of a blind spot (such as a form of a recess), a shape of a cross section of a retina (such as a shape of unevenness)), nature characteristics (such as a position of a fovea, a position of a blind spot, and a feature of, for example, an affected region), and optical characteristics (such as refraction in an eyeball and an aberration of the eyeball). The processor 191 may define a coordinate system on the basis of a distribution of characteristics of an eyeball. Note that, for example, a definition section that defines a coordinate system may be provided to the controller 112 independently from the processor 191 without a coordinate system being defined by the processor 191 on the basis of a distribution of characteristics of an eyeball. The coordinate system is defined on the basis of at least two selected from the group consisting of a right-eye first fovea, a right-eye first blind spot, a left-eye second fovea, and a left-eye second blind spot. A displayed video and a display position are defined using the coordinate system. This results in smaller volumes of data, compared to when a pattern map is used. Further, a displayed video and a display position may be controlled in the processor 191 on the basis of information regarding a rotation of an eyeball. This results in less intensive processing, compared to when pattern matching is used.

The matching section 192 performs matching on a distribution of characteristics of an eyeball and a state of the eyeball. For example, using the coordinate system described above, the matching section 192 performs matching on a distribution of characteristics of an eyeball and a state of the eyeball to which a video is to be presented (the eyeball to which a video is to be presented may be referred to as a concerned eye). The matching section 192 acquires a deviation of a visual axis from an optical axis (gaze calibration), and can generate a map in which an offset is reflected.

The display apparatus of the first embodiment according to the present technology (the first example of the display apparatus) has been described above. Unless there is a technical inconsistency in particular, contents of the description can be applied to the display apparatus of the second embodiment according to the present technology (a second example of the display apparatus), a display method of a third embodiment according to the present technology (a first example of a display method), and a display method of a fourth embodiment according to the present technology (a second example of the display method). These will be described later.

3. Second Embodiment (Second Example of Display Apparatus)

The display apparatus of the second embodiment according to the present technology (the second example of the display apparatus) is a display apparatus that includes a light source, a processor that performs processing on a distribution of characteristics of an eyeball, a monitoring section that monitors a state of the eyeball, a matching section that performs matching on the distribution of the characteristics of the eyeball and the state of the eyeball, and an irradiator that irradiates a specified position on a retina with video display light emitted by the light source, and that further includes an acquisition section that acquires the distribution of the characteristics of the eyeball. In other words, the display apparatus of the second embodiment according to the present technology is a display apparatus obtained by adding, to the display apparatus of the first embodiment according to the present technology, the acquisition section acquiring a distribution of characteristics of an eyeball. The display apparatus of the second embodiment according to the present technology may further include a follower. The display apparatus of the second embodiment according to the present technology can be applied to, for example, an eyewear display and a head-mounted display.

The processor performing processing on a distribution of characteristics of an eyeball performs processing on, for example, information regarding a distribution of characteristics of an eyeball, the information regarding a distribution of characteristics of an eyeball being obtained from the acquisition section (such as a fundus camera, an OCT, a light detection apparatus that detects light that returns due to IR scanning, or a refractometer). The monitoring section monitors a state of an eyeball using, for example, a corneal reflex or a fundus reflex, and can acquire an optical axis. The matching section acquires a deviation of a visual axis from the optical axis (gaze calibration), and can generate a map in which an offset is reflected. The irradiator can modulate light depending on the laser source, display of a video (a projector), and a distribution of characteristics of an eyeball, can adjust a light amount depending on external light, and can perform control including distortion correction. The follower can cause a displayed video to follow an ocular movement due to eye tracking, where a light ray is steered to change an irradiated video and an irradiation position on the basis of information regarding a rotation of an eyeball.

An example of a configuration of the display apparatus of the second embodiment according to the present technology is described with reference to FIG. 12.

Figure 12:
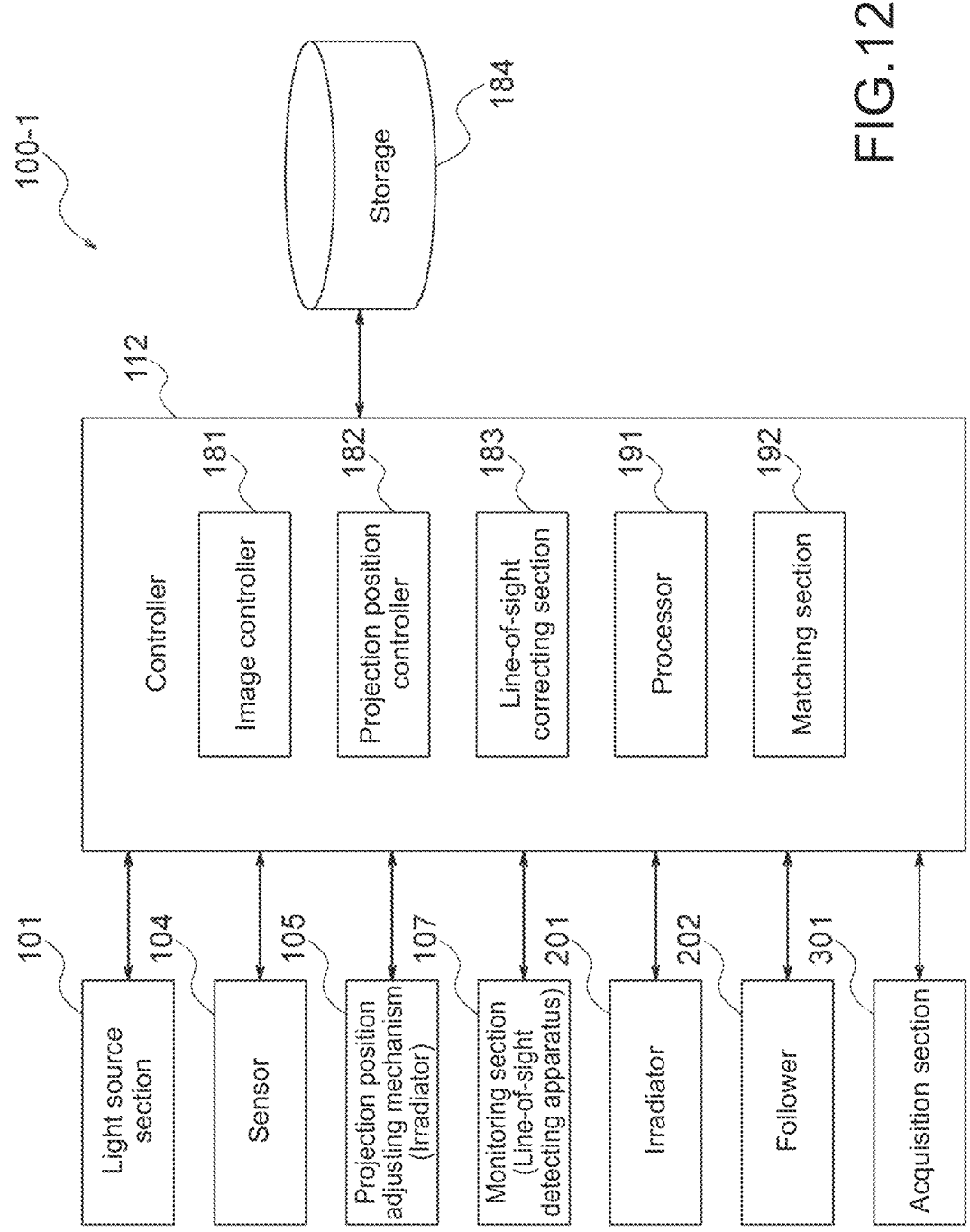
FIG. 12 is a block diagram illustrating an example of a configuration of a display apparatus of a second embodiment to which the present technology has been applied.

FIG. 12 is a block diagram illustrating primary structural elements of the display apparatus of the second embodiment according to the present technology (the display apparatus 100-1).

The display apparatus 100-1 includes the light source section 101, the sensor 104, the projection position adjusting mechanism 105 serving as an irradiator, the monitoring section (a line-of-sight detecting mechanism) 107, the irradiator 201 including a see-through member arranged in front of the eyes (such as a reflective or transmissive volume hologram or a reflective or transmissive relief hologram), the follower 202, an acquisition section 301, and the controller 112. Note that the display apparatus 100-1 does not necessarily have to include the follower 202.

The controller 112 includes the image controller 181, the projection position controller 182, the line-of-sight correcting section 183, the processor 191, and the matching section 192.

The image controller 181 controls projection of video display light that is performed by the video display section. For example, the image controller 181 drives the light source sections 101L and 101R, that is, the image controller 181 drives in particular the laser sources and scanning mirrors included in these light source sections, and causes the light source sections to output pieces of video display light. For example, the image controller 181 may acquire image data stored in the storage 184, and may cause the light source sections 101L and 101R to output pieces of video display light on the basis of the acquired image data. The image controller 181 may correct the image data on the basis of a change in the position of the display apparatus 100 relative to the head of a user, the change being detected by the sensor 104. On the basis of the image data after the correction, the image controller 181 may cause the light source sections 101L and 101R to output pieces of video display light. In other words, the display apparatus 100 may correct an image on the basis of a change in the position of the display apparatus relative to the head of a user, the positional change being detected by a sensor that detects the positional change.

The projection position controller 182 controls the projection position adjusting mechanisms 105L-1, 105L-2, 105R-1, and 105R-2, and this results in being able to control a projection position of video display light. For example, the projection position controller 182 may adjust the projection position of video display light by driving one of, two of, three of, or four of the projection position adjusting mechanisms 105L-1, 105L-2, 105R-1, and 105R-2 on the basis of a line of sight detected by the monitoring sections 107L and 107R. For example, the projection position of video display light may be adjusted such that the video display light follows the line of sight. The projection position controller 182 may adjust the projection position of video display light by driving one of, two of, three of, or four of the projection position adjusting mechanisms 105L-1, 105L-2, 105R-1, and 105R-2 on the basis of the line of sight after correction performed by the line-of-sight correcting section 183, which will be described later. For example, the projection position of video display light may be adjusted such that the video display light follows the line of sight after the correction. The projection position controller 182 may adjust the projection position of video display light by driving one of, two of, three of, or four of the projection position adjusting mechanisms 105L-1, 105L-2, 105R-1, and 105R-2 on the basis of data (hereinafter also referred to as "displacement data") related to a change in the position of the display apparatus 100 relative to the head of a user, the change being detected by one of, two of, three of, or four of the sensors 104L, 104R, 104C, and 104T.

For example, the projection position controller 182 may calculate an amount of positional adjustment performed by each projection position adjusting mechanism on the basis of the displacement data and a correction coefficient. The projection position controller 182 may drive each projection position adjusting mechanism such that a positional relationship is changed by the calculated amount of positional adjustment. For example, the projection position controller 182 may acquire a correction coefficient from a correction table stored in the storage 184 in advance, and may use the acquired correction coefficient in order to calculate the amount of positional adjustment. For example, the correction table may include a plurality of correction coefficients, and the projection position controller 182 may select a specified correction coefficient from the plurality of correction coefficients according to the displacement data. Further, for example, the correction table may be provided for each projection position adjusting mechanism. The correction table may be included in the display apparatus 100 in advance, or may be updated in response to the display apparatus 100 being used by a user. The selection or the update of a correction table or a correction coefficient makes it possible to improve the accuracy in controlling a projection position. In order to calculate the amount of positional adjustment, the projection position controller 182 may use a line of sight detected by the monitoring section, or a line of sight after correction performed by the line-of-sight correcting section 183.

The line-of-sight correcting section 183 corrects a line of sight detected by the monitoring sections 107L and 107R, on the basis of the displacement data. This enables the line-of-sight correcting section 183 to identify a line of sight in consideration of a state of being worn with an offset, and this results in improving the accuracy in detecting a line of sight. The correction may be performed with respect to an optical axis of an eyeball, may be performed with respect to a visual axis of the eyeball, or may be performed with respect to a reference axis other than the optical axis and the visual axis. Likewise, the line-of-sight correcting section 183 may acquire a correction coefficient from a correction table stored in the storage 184 in advance, and may use the acquired correction coefficient in order to correct a line of sight. For example, the correction table may include a plurality of correction coefficients, and the line-of-sight correcting section 183 may select a specified correction coefficient from the plurality of correction coefficients according to the displacement data. The correction table may be included in the display apparatus 100 in advance, or may be updated in response to the head-mounted display apparatus 100 being used by a user. The selection or the update of a correction table or a correction coefficient makes it possible to improve the accuracy in correcting a line of sight.

The display apparatus 100 may further include the storage 184. The storage may store therein data related to video display light projected by the video display section, a correction table used by the projection position controller 122 to control a projection position, and a correction table used by the line-of-sight correcting section 123 to correct a line of sight.

The processor 191 performs processing on information regarding a distribution of characteristics of an eyeball. For example, the distribution of characteristics of an eyeball may be acquired from the acquisition section 301. For example, the distribution of characteristics of an eyeball is acquired using a fundus camera included in the acquisition section 301, or is acquired using an OCT, a refractometer, or a light detection apparatus that detects light that returns due to IR scanning, the OCT, the refractometer, or the light detection apparatus being included in the acquisition section 301. The distribution of characteristics of an eyeball may be acquired from shape characteristics (such as a size and a shape of an eyeball, a size and a shape of a macula (such as a form of a recess), a size and a shape of a blind spot (such as a form of a recess), a shape of a cross section of a retina (such as a shape of unevenness)), nature characteristics (such as a position of a fovea, a position of a blind spot, and a feature of, for example, an affected region), and optical characteristics (such as refraction in an eyeball and an aberration of the eyeball). The processor 191 may define a coordinate system on the basis of a distribution of characteristics of an eyeball. Note that, for example, a definition section that defines a coordinate system may be provided to the controller 112 independently from the processor 191 without a coordinate system being defined by the processor 191 on the basis of a distribution of characteristics of an eyeball. The coordinate system is defined on the basis of at least two selected from the group consisting of a right-eye first fovea, a right-eye first blind spot, a left-eye second fovea, and a left-eye second blind spot. A displayed video and a display position are defined using the coordinate system. This results in smaller volumes of data, compared to when a pattern map is used. Further, a displayed video and a display position may be controlled in the processor 191 on the basis of information regarding a rotation of an eyeball. This results in less intensive processing, compared to when pattern matching is used.

The matching section 192 performs matching on a distribution of characteristics of an eyeball and a state of the eyeball. For example, using the coordinate system described above, the matching section 192 performs matching on a distribution of characteristics of an eyeball and a state of the eyeball to which a video is to be presented (the eyeball to which a video is to be presented may be referred to as a concerned eye). The matching section 192 acquires a deviation of a visual axis from an optical axis (gaze calibration), and can generate a map in which an offset is reflected.

4. Third Embodiment (First Example of Display Method)

The display method of the third embodiment according to the present technology (the first example of the display method) is a display method that includes performing processing on a distribution of characteristics of an eyeball, monitoring a state of the eyeball, performing matching on the distribution of the characteristics of the eyeball and the state of the eyeball, and irradiating a specified position on a retina with video display light emitted by a light source.

The display method of the third embodiment according to the present technology (the first example of the display method) is performed using the display apparatus of the first embodiment according to the present technology (the first example of the display apparatus) (such as the display apparatus 100).

Further, contents described with reference to FIGS. 1 and 5 described above may be applied to a flow of the display method of the third embodiment according to the present technology (the first example of the display method). Note that Step S101 (taking an eyeground photo when an eyeball is viewed from the front), Step S102 (taking an eyeground photo when an eyeball is rotated leftward, rightward, upward, or downward), and Step S103 (detecting positions of a fovea and a blind spot in the respective eyeground photos) of FIG. 1; and Step S201 (generating an eyeground map) and Step S202 (acquiring characteristics of an eyeball) of FIG. 5 may be performed using an external apparatus (such as a fundus camera, an OCT, or a refractometer) other than the display apparatus of the first embodiment according to the present technology (the first example of the display apparatus) (such as the display apparatus 100).

5. Fourth Embodiment (Second Example of Display Method)

The display method of the fourth embodiment according to the present technology (the second example of the display method) is a display method that includes performing processing on a distribution of characteristics of an eyeball, monitoring a state of the eyeball, performing matching on the distribution of the characteristics of the eyeball and the state of the eyeball, and irradiating a specified position on a retina with video display light emitted by a light source, and that further includes acquiring the distribution of the characteristics of the eyeball. In other words, the display method of the fourth embodiment according to the present technology is a display method obtained by adding the acquiring a distribution of characteristics of an eyeball to the display method of the third embodiment according to the present technology.

The display method of the fourth embodiment according to the present technology (the second example of the display method) is performed using the display apparatus of the second embodiment according to the present technology (the second example of the display apparatus) (such as the display apparatus 100-1).

The contents described with reference to FIGS. 1 and 5 described above may be applied to a flow of the display method of the fourth embodiment according to the present technology (the second example of the display method).

Note that embodiments according to the present technology are not limited to the embodiments described above, and various modifications may be made thereto without departing from the scope of the present technology.

Further, the effects described herein are not limitative but are merely illustrative, and other effects may be provided.

Further, the present technology may also take the following configurations.

(1) A display apparatus, including:
    a light source;
    a processor that performs processing on a distribution of characteristics of an eyeball;
    a monitoring section that monitors a state of the eyeball;
    a matching section that performs matching on the distribution of the characteristics of the eyeball and the state of the eyeball; and
    an irradiator that irradiates a specified position on a retina with video display light emitted by the light source.

(2) The display apparatus according to (1), further including
    an acquisition section that acquires the distribution of the characteristics of the eyeball.

(3) The display apparatus according to (2), in which
    the acquisition section includes at least one selected from the group consisting of a fundus camera, an OCT, a refractometer, and a light detection apparatus that detects light that returns due to IR scanning.

(4) The display apparatus according to any one of (1) to (3), in which
    the monitoring section monitors the state of the eyeball using a corneal reflex or a fundus reflex.

(5) The display apparatus according to any one of (1) to (4), further including
    a follower that causes the video display light to follow a movement of the eyeball.

(6) The display apparatus according to (5), in which
    the follower includes at least one selected from the group consisting of a combiner, a relay-system drive section, a mirror drive section, and a phase difference panel.

(7) The display apparatus according to any one of (1) to (6), in which a coordinate system is defined on the basis of the distribution of the characteristics of the eyeball, and
using the coordinate system, the matching section performs matching on the distribution of the characteristics of the eyeball and the state of the eyeball to which a video is to be presented.

(8) The display apparatus according to (7), in which
the coordinate system is defined on the basis of at least two selected from the group consisting of a right-eye first fovea, a right-eye first blind spot, a left-eye second fovea, and a left-eye second blind spot.

(9) The display apparatus according to any one of (1) to (8), in which
the light source is a laser source.

(10) The display apparatus according to any one of (1) to (9), further including
a scanning mirror, in which
the scanning mirror irradiates the video display light onto the retina.

(11) The display apparatus according to any one of (1) to (10), in which
the irradiator further includes a member arranged in front of eyes, and
the member is a see-through member.

(12) The display apparatus according to (11), in which
the member is a first optical element or a second optical element, the first optical element including a reflective or transmissive volume hologram, a reflective or transmissive relief hologram, or a meta-surface, the second optical element being an optical element off which specified light is reflected and through which light other than the specified light is transmitted.

(13) The display apparatus according to any one of (1) to (12), further including
a member for compensating for a wavelength dispersion.

(14) The display apparatus according to (13), in which
the member for compensating for a wavelength dispersion is a first optical element that includes a reflective or transmissive volume hologram, a reflective or transmissive relief hologram, or a meta-surface.

(15) A display method, including:
performing processing on a distribution of characteristics of an eyeball;
monitoring a state of the eyeball;
performing matching on the distribution of the characteristics of the eyeball and the state of the eyeball; and
irradiating a specified position on a retina with video display light emitted by a light source.

(16) The display method according to (15), further including
acquiring the distribution of the characteristics of the eyeball.

(17) The display method according to (16), in which
the acquiring the distribution of the characteristics of the eyeball includes acquiring the distribution of the characteristics of the eyeball using at least one selected from the group consisting of an OCT, a refractometer, and a light detection apparatus that detects light that returns due to IR scanning.

(18) The display method according to any one of (15) to (17), in which
the monitoring the state of the eyeball includes monitoring the state of the eyeball using a corneal reflex or a fundus reflex.

(19) The display method according to any one of (15) to (18), further including
causing the video display light to follow a movement of the eyeball.

(20) The display method according to (19), in which
the causing the video display light to follow the movement of the eyeball includes causing the video display light to follow the movement of the eyeball using at least one selected from the group consisting of a combiner, a relay-system drive section, a mirror drive section, and a phase difference panel.

(21) The display method according to any one of (15) to (20), further including
defining a coordinate system on the basis of the distribution of the characteristics of the eyeball, in which
the performing matching on the distribution of the characteristics of the eyeball and the state of the eyeball includes performing matching on the distribution of the characteristics of the eyeball and the state of the eyeball to which a video is to be presented, using the coordinate system.

(22) The display method according to (21), in which
the coordinate system is defined on the basis of at least two selected from the group consisting of a right-eye first fovea, a right-eye first blind spot, a left-eye second fovea, and a left-eye second blind spot.

(23) The display method according to any one of (15) to (22), in which
the light source is a laser source.

(24) The display method according to any one of (15) to (23), in which
irradiating the video display light onto the retina using a scanning mirror is included.

(25) The display method according to any one of (15) to (24), further including:
providing a see-through member; and
arranging the see-through member in front of eyes.

(26) The display method according to (25), in which
the member is a first optical element or a second optical element, the first optical element including a reflective or transmissive volume hologram, a reflective or transmissive relief hologram, or a meta-surface, the second optical element being an optical element off which specified light is reflected and through which light other than the specified light is transmitted.

(27) The display method according to any one of (15) to (26), further including
providing a member for compensating for a wavelength dispersion.

(28) The display method according to (27), in which
the member for compensating for a wavelength dispersion is a first optical element that includes a reflective or transmissive volume hologram, a reflective or transmissive relief hologram, or a meta-surface.

REFERENCE SIGNS LIST 1 optical axis (optical vector)
2 visual axis (gaze vector)
10 pupil
20 eyeball
30 fovea
31 blind spot
100, 100-1 display apparatus
101 light source section
104 sensor
105 projection position adjusting mechanism 107 monitoring section (line-of-sight detecting apparatus)
112 controller
181 image controller
182 projection position controller
183 line-of-sight correcting section
191 processor
192 matching section
201 irradiator
201 follower
301 acquisition section

What is claimed is:

1. A display apparatus, comprising:
a light source;
a processor that performs processing on a distribution of characteristics of an eyeball;
a monitoring section that monitors a state of the eyeball;
a matching section that performs matching on the distribution of the characteristics of the eyeball and the state of the eyeball; and
an irradiator that irradiates a specified position on a retina with video display light emitted by the light source,
wherein a coordinate system is defined on a basis of the distribution of the characteristics of the eyeball, and
wherein using the coordinate system, the matching section performs matching on the distribution of the characteristics of the eyeball and the state of the eyeball to which a video is to be presented.

2. The display apparatus according to claim 1, further comprising an acquisition section that acquires the distribution of the characteristics of the eyeball.

3. The display apparatus according to claim 2, wherein the acquisition section includes at least one selected from the group consisting of a fundus camera, an OCT, a refractometer, and a light detection apparatus that detects light that returns due to IR scanning.

4. The display apparatus according to claim 1, wherein the monitoring section monitors the state of the eyeball using a corneal reflex or a fundus reflex.

5. The display apparatus according to claim 1, further comprising a follower that causes the video display light to follow a movement of the eyeball.

6. The display apparatus according to claim 5, wherein the follower includes at least one selected from the group consisting of a combiner, a relay-system drive section, a mirror drive section, and a phase difference panel.

7. The display apparatus according to claim 1, wherein the coordinate system is defined on a basis of at least two selected from the group consisting of a right-eye first fovea, a right-eye first blind spot, a left-eye second fovea, and a left-eye second blind spot.

8. The display apparatus according to claim 1, wherein the light source is a laser source.

9. The display apparatus according to claim 1, further comprising:
a scanning mirror, wherein
the scanning mirror irradiates the video display light onto the retina.

10. The display apparatus according to claim 1, wherein the irradiator further includes a member arranged in front of eyes, and the member is a see-through member.

11. The display apparatus according to claim 10, wherein the member is a first optical element or a second optical element, the first optical element including a reflective or transmissive volume hologram, a reflective or transmissive relief hologram, or a meta-surface, the second optical element being an optical element off which specified light is reflected and through which light other than the specified light is transmitted.

12. The display apparatus according to claim 1, further comprising a member for compensating for a wavelength dispersion.

13. The display apparatus according to claim 12, wherein the member for compensating for a wavelength dispersion is a first optical element that includes a reflective or transmissive volume hologram, a reflective or transmissive relief hologram, or a meta-surface.

14. A display method, comprising:
performing processing on a distribution of characteristics of an eyeball;
monitoring a state of the eyeball;
performing matching on the distribution of the characteristics of the eyeball and the state of the eyeball; and
irradiating a specified position on a retina with video display light emitted by a light source,
wherein a coordinate system is defined on a basis of the distribution of the characteristics of the eyeball, and
wherein using the coordinate system matching is performed on the distribution of the characteristics of the eyeball and the state of the eyeball to which a video is to be presented.

15. The display method according to claim 14, further comprising acquiring the distribution of the characteristics of the eyeball.

* * * * *